US010850098B2

(12) United States Patent
Glukhovsky et al.

(10) Patent No.: US 10,850,098 B2
(45) Date of Patent: *Dec. 1, 2020

(54) SYSTEMS AND APPARATUS FOR GAIT MODULATION AND METHODS OF USE

(71) Applicant: Bioness Inc., Valencia, CA (US)

(72) Inventors: Arkady Glukhovsky, Valencia, CA (US); Keith McBride, Ventura, CA (US)

(73) Assignee: Bioness Inc., Valencia, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/146,368

(22) Filed: Sep. 28, 2018

(65) Prior Publication Data

US 2019/0167986 A1 Jun. 6, 2019

Related U.S. Application Data

(60) Continuation of application No. 15/872,634, filed on Jan. 16, 2018, now Pat. No. 10,086,196, which is a
(Continued)

(51) Int. Cl.
*A61N 1/36* (2006.01)
*A61B 5/11* (2006.01)
(Continued)

(52) U.S. Cl.
CPC .......... *A61N 1/36003* (2013.01); *A61B 5/112* (2013.01); *A61B 5/4836* (2013.01);
(Continued)

(58) Field of Classification Search
CPC ............... A61N 1/36003; A61N 1/36
(Continued)

(56) References Cited

U.S. PATENT DOCUMENTS 3,204,637 A 9/1965 Frank et al.
3,344,792 A 10/1967 Offner et al.
(Continued)

FOREIGN PATENT DOCUMENTS

DE 19830359 A1 1/2000
EP 1508302 2/2005
(Continued)

OTHER PUBLICATIONS

Examination Report for Australian Application No. 2015236546, dated Feb. 8, 2019, 4 pages.
(Continued)

*Primary Examiner* — Nadia A Mahmood
(74) *Attorney, Agent, or Firm* — Cooley LLP

(57) ABSTRACT

An apparatus includes a frame, a sensor, and an electric stimulator. The frame is removably couplable to a portion of a limb. The sensor is configured to produce a first signal associated with a gait characteristic at a first time, and a second signal associated with the gait characteristic at a second time, after the first time. The electric stimulator is removably coupled to the frame and is in electrical communication with an electrode assembly and the sensor to receive the first signal substantially at the first time and the second signal substantially at the second time. Based in part on the gait characteristic at the first time, the electric stimulator sends a third signal to the electrode assembly to provide an electric stimulation to a portion of a neuromuscular system of the limb substantially during a time period defined between the first time and the second time.

18 Claims, 10 Drawing Sheets

Related U.S. Application Data division of application No. 14/223,340, filed on Mar. 24, 2014, now Pat. No. 9,867,985.

(51) Int. Cl.
*A61B 5/00* (2006.01)
*A61B 5/103* (2006.01)
*A61F 5/01* (2006.01)
*A61N 1/04* (2006.01)

(52) U.S. Cl.
CPC .......... *A61B 5/4851* (2013.01); *A61B 5/6811* (2013.01); *A61B 5/1038* (2013.01); *A61B 5/6807* (2013.01); *A61B 5/6828* (2013.01); *A61F 5/01* (2013.01); *A61N 1/0452* (2013.01); *A61N 1/0484* (2013.01)

(58) Field of Classification Search
USPC ...................................................... 607/49, 2
See application file for complete search history.

(56) References Cited

U.S. PATENT DOCUMENTS

| | | |
|---|---|---|
| 3,426,748 A | 2/1969 | Bowers |
| 3,881,496 A | 5/1975 | Vredenbregt et al. |
| 3,941,137 A | 3/1976 | Vredenbregt et al. |
| 4,381,012 A | 4/1983 | Russek |
| 4,432,368 A | 2/1984 | Russek |
| 4,528,984 A | 7/1985 | Morawetz et al. |
| 4,558,704 A | 12/1985 | Petrofsky |
| 4,569,352 A | 2/1986 | Petrofsky et al. |
| 4,580,569 A | 4/1986 | Petrofsky |
| 4,586,495 A | 5/1986 | Petrofsky |
| 4,647,918 A | 3/1987 | Goforth |
| 4,697,808 A | 10/1987 | Larson et al. |
| 4,745,930 A | 5/1988 | Confer |
| 4,832,033 A | 5/1989 | Maher et al. |
| 4,976,264 A | 12/1990 | Petrofsky |
| 4,996,987 A | 3/1991 | Petrofsky |
| 5,016,635 A | 5/1991 | Graupe |
| 5,081,989 A | 1/1992 | Graupe et al. |
| 5,112,296 A | 5/1992 | Beard et al. |
| 5,121,747 A | 6/1992 | Andrews |
| 5,167,229 A | 12/1992 | Peckham et al. |
| 5,253,654 A | 10/1993 | Thomas et al. |
| 5,277,697 A | 1/1994 | France et al. |
| 5,285,781 A | 2/1994 | Brodard |
| 5,300,096 A | 4/1994 | Hall et al. |
| 5,318,597 A | 6/1994 | Hauck et al. |
| 5,323,650 A | 6/1994 | Fullen et al. |
| 5,330,516 A | 7/1994 | Nathan |
| 5,350,414 A | 9/1994 | Kolen |
| 5,357,696 A | 10/1994 | Gray et al. |
| 5,408,873 A | 4/1995 | Schmidt et al. |
| 5,433,737 A | 7/1995 | Aimone |
| 5,437,619 A | 8/1995 | Malewicz et al. |
| 5,476,441 A | 12/1995 | Durfee et al. |
| 5,487,759 A | 1/1996 | Bastyr et al. |
| 5,540,735 A | 7/1996 | Wingrove |
| 5,562,707 A | 10/1996 | Prochazka et al. |
| 5,566,479 A | 10/1996 | Gray et al. |
| 5,628,722 A | 5/1997 | Solomonow et al. |
| 5,643,332 A | 7/1997 | Stein |
| 5,664,346 A | 9/1997 | Barker |
| 5,724,996 A | 3/1998 | Piunti |
| 5,748,845 A | 5/1998 | Labun et al. |
| 5,775,332 A | 7/1998 | Goldman |
| 5,814,093 A | 9/1998 | Stein |
| 5,843,142 A | 12/1998 | Sultan |
| 5,851,191 A | 12/1998 | Gozani |
| 5,861,017 A | 1/1999 | Smith et al. |
| 5,916,159 A | 6/1999 | Kelly et al. |
| 5,951,598 A | 9/1999 | Bishay et al. |
| 5,980,472 A | 11/1999 | Seyl |
| 5,983,140 A | 11/1999 | Smith et al. |
| 6,002,965 A | 12/1999 | Katz et al. |
| 6,064,912 A | 5/2000 | Kenney |
| 6,126,355 A | 10/2000 | Clover, Jr. |
| 6,129,695 A | 10/2000 | Peters et al. |
| 6,174,294 B1 | 1/2001 | Crabb et al. |
| 6,195,921 B1 | 3/2001 | Truong |
| 6,236,890 B1 | 5/2001 | Oldham |
| 6,246,863 B1 | 6/2001 | Kampel |
| 6,261,247 B1 | 7/2001 | Ishikawa et al. |
| 6,282,448 B1 | 8/2001 | Katz et al. |
| 6,308,102 B1 | 10/2001 | Sieracki et al. |
| 6,349,126 B2 | 2/2002 | Ogawa et al. |
| 6,379,313 B1 | 4/2002 | Gozani |
| 6,445,955 B1 | 9/2002 | Michelson et al. |
| 6,456,884 B1 | 9/2002 | Kenney |
| 6,456,885 B1 | 9/2002 | Shiba et al. |
| 6,496,739 B2 | 12/2002 | Arbel |
| 6,507,757 B1 | 1/2003 | Swain et al. |
| 6,516,500 B2 | 2/2003 | Ogino et al. |
| 6,564,103 B2 | 5/2003 | Fischer et al. |
| 6,567,706 B2 | 5/2003 | Bar-Or et al. |
| 6,571,115 B2 | 5/2003 | Axelgaard et al. |
| 6,607,500 B2 | 8/2003 | Da Silva et al. |
| 6,651,352 B2 | 11/2003 | McGorry et al. |
| 6,700,499 B2 | 3/2004 | Kubo et al. |
| 6,701,189 B2 | 3/2004 | Fang et al. |
| D494,273 S | 8/2004 | Haugland et al. |
| 6,788,979 B1 | 9/2004 | Axelgaard et al. |
| 6,829,510 B2 | 12/2004 | Nathan et al. |
| 6,836,744 B1 | 12/2004 | Asphahani et al. |
| 6,978,684 B2 | 12/2005 | Nurse |
| 6,988,005 B2 | 1/2006 | McGraw et al. |
| 7,146,220 B2 | 12/2006 | Dar et al. |
| 7,162,305 B2 | 1/2007 | Tong et al. |
| 7,200,517 B2 | 4/2007 | Darley et al. |
| 7,257,448 B2 | 8/2007 | Crowe et al. |
| 7,337,007 B2 | 2/2008 | Nathan et al. |
| 7,359,751 B1 | 4/2008 | Erickson et al. |
| 7,403,821 B2 | 7/2008 | Haugland et al. |
| 7,410,471 B1 | 8/2008 | Campbell et al. |
| 7,416,537 B1 | 8/2008 | Stark et al. |
| 7,537,573 B2 | 5/2009 | Horst |
| 7,632,239 B2 | 12/2009 | Dar et al. |
| 7,713,217 B2 | 5/2010 | Ikeuchi et al. |
| 7,756,585 B2 | 7/2010 | Embrey et al. |
| 7,785,279 B2 | 8/2010 | Sankai |
| 7,899,556 B2 | 3/2011 | Nathan et al. |
| 8,070,703 B2 | 12/2011 | Skahan et al. |
| 8,209,022 B2 | 6/2012 | Dar et al. |
| 8,209,036 B2 | 6/2012 | Nathan et al. |
| 8,382,688 B2 | 2/2013 | Dar et al. |
| 8,694,110 B2 | 4/2014 | Nathan et al. |
| 8,788,049 B2 | 7/2014 | Lasko et al. |
| 8,868,217 B2 | 10/2014 | Dar et al. |
| 8,972,017 B2 | 3/2015 | Dar et al. |
| 9,095,417 B2 | 8/2015 | Dar et al. |
| 9,415,202 B2 | 8/2016 | Solomon et al. |
| 9,415,205 B2 | 8/2016 | Lasko et al. |
| 9,867,985 B2 | 1/2018 | Glukhovsky et al. |
| 10,016,598 B2 | 7/2018 | Lasko et al. |
| 10,076,656 B2 | 9/2018 | Dar et al. |
| 10,080,885 B2 | 9/2018 | Nathan et al. |
| 2002/0077688 A1 | 6/2002 | Kirkland |
| 2003/0014087 A1 | 1/2003 | Fang et al. |
| 2003/0065368 A1 | 4/2003 | Van Der Hoeven |
| 2003/0083596 A1 | 5/2003 | Kramer et al. |
| 2003/0114894 A1 | 6/2003 | Dar et al. |
| 2004/0011366 A1 | 1/2004 | Schulman et al. |
| 2004/0015203 A1 | 1/2004 | McGraw et al. |
| 2004/0044381 A1 | 3/2004 | Duncan et al. |
| 2004/0082979 A1 | 4/2004 | Tong et al. |
| 2004/0122483 A1 | 6/2004 | Nathan et al. |
| 2004/0133081 A1 | 7/2004 | Teller et al. |
| 2004/0147975 A1 | 7/2004 | Popovic et al. |
| 2004/0172097 A1 | 9/2004 | Brodard et al. |
| 2004/0173220 A1 | 9/2004 | Harry et al. |
| 2004/0243197 A1 | 12/2004 | Demian |
| 2004/0249316 A1 | 12/2004 | Ashihara et al. |

(56) References Cited

U.S. PATENT DOCUMENTS

| | | |
|---|---|---|
| 2004/0254624 A1 | 12/2004 | Johnson |
| 2005/0043660 A1 | 2/2005 | Stark et al. |
| 2005/0049652 A1 | 3/2005 | Tong |
| 2005/0085704 A1 | 4/2005 | Schulz et al. |
| 2005/0131317 A1 | 6/2005 | Oddsson et al. |
| 2005/0192645 A1 | 9/2005 | Stein et al. |
| 2005/0261609 A1 | 11/2005 | Collings et al. |
| 2006/0015470 A1 | 1/2006 | Lauer et al. |
| 2006/0020421 A1 | 1/2006 | Darley et al. |
| 2006/0111756 A1 | 5/2006 | Chang |
| 2006/0211956 A1 | 9/2006 | Sankai |
| 2006/0276704 A1 | 12/2006 | McGinnis et al. |
| 2006/0282017 A1 | 12/2006 | Avni et al. |
| 2006/0282018 A1 | 12/2006 | Balzano |
| 2007/0021689 A1 | 1/2007 | Stergiou et al. |
| 2007/0106343 A1 | 5/2007 | Monogue et al. |
| 2007/0123756 A1 | 5/2007 | Kitajima et al. |
| 2007/0130893 A1 | 6/2007 | Davies |
| 2007/0179560 A1 | 8/2007 | Tong et al. |
| 2007/0197946 A1 | 8/2007 | Gilmour |
| 2007/0203533 A1 | 8/2007 | Goren et al. |
| 2008/0033505 A1 | 2/2008 | Davis et al. |
| 2008/0045872 A1 | 2/2008 | Bauerfeind et al. |
| 2008/0140154 A1 | 6/2008 | Loeb et al. |
| 2008/0154335 A1 | 6/2008 | Thrope et al. |
| 2008/0177355 A1 | 7/2008 | Miesel et al. |
| 2008/0294080 A1 | 11/2008 | Adarraga |
| 2008/0319349 A1 | 12/2008 | Zilberman |
| 2009/0012436 A1 | 1/2009 | Lanfermann et al. |
| 2009/0043357 A1 | 2/2009 | Tong et al. |
| 2009/0149917 A1 | 6/2009 | Whitehurst et al. |
| 2011/0137375 A1 | 6/2011 | McBride |
| 2012/0059432 A1 | 3/2012 | Emborg et al. |
| 2012/0203156 A1 | 8/2012 | Dar et al. |
| 2013/0131555 A1 | 5/2013 | Hook et al. |
| 2014/0135858 A1 | 5/2014 | Ahmed et al. |
| 2014/0180361 A1 | 6/2014 | Burdick et al. |
| 2014/0303705 A1 | 10/2014 | Nathan et al. |
| 2015/0080979 A1 | 3/2015 | Lasko et al. |
| 2015/0265834 A1 | 9/2015 | Glukhovsky et al. |
| 2015/0273205 A1 | 10/2015 | Dar et al. |
| 2015/0321000 A1 | 11/2015 | Rosenbluth et al. |
| 2018/0140833 A1 | 5/2018 | Glukhovsky et al. |
| 2018/0318583 A1 | 11/2018 | McBride |
| 2019/0009086 A1 | 1/2019 | Lasko et al. |
| 2019/0151649 A1 | 5/2019 | Dar et al. |
| 2019/0167975 A1 | 6/2019 | Nathan et al. |

FOREIGN PATENT DOCUMENTS

| | | | |
|---|---|---|---|
| GB | | 2474239 A | 4/2011 |
| JP | | 1985-119949 A | 6/1985 |
| JP | | H05-293188 A | 11/1993 |
| JP | | 1994-501854 T | 3/1994 |
| JP | | H06-501854 | 3/1994 |
| JP | | 2002-191580 A | 7/2002 |
| JP | | 2002-200104 | 7/2002 |
| JP | | 2004-503266 T | 2/2004 |
| JP | | 2004-215735 A | 8/2004 |
| JP | | 2004-313555 A | 11/2004 |
| JP | | 2005-514143 T | 5/2005 |
| JP | | 2006-166244 A | 6/2006 |
| JP | | 2006-192276 | 7/2006 |
| JP | | 2009-530064 | 8/2009 |
| WO | WO | 2003/051453 | 6/2003 |
| WO | WO | 2004/098703 | 11/2004 |
| WO | WO | 2008/005865 | 1/2008 |
| WO | WO | 2014/030295 | 2/2014 |
| WO | WO | 2015/188889 A1 | 12/2015 |

OTHER PUBLICATIONS

Office Action for Japanese Application No. 2016-547617, dated Jan. 7, 2019 and English translation.

Feng, C. J. et al., "Three-Dimensional Motion Analysis of the Voluntary Elbow Movement in Subjects with Spasticity," IEEE Transactions on Rehabilitation Engineering, 5(3):253-262, 1997.

Office Action for Australian Patent Application No. 2006236428, dated Jan. 25, 2010.

Office Action for European Patent Application No. 06750483.7, dated Apr. 16, 2009, 5 pages.

International Search Report and Written Opinion for PCT/US06/014455, dated Aug. 8, 2006.

Supplementary European Search Report for European Application No. 10835019.0, dated Feb. 12, 2014.

Office Action for U.S. Appl. No. 12/630,199, dated Jun. 21, 2011.

Office Action for U.S. Appl. No. 12/630,199, dated Jan. 18, 2012.

Examiner's Answer to Appeal Brief for U.S. Appl. No. 12/630,199, dated Aug. 14, 2012.

International Search Report and Written Opinion for International Application No. PCT/US2010/058483, dated Feb. 7, 2011.

Examination Report for Australian Application No. 2006314072, dated May 5, 2010, 4 pages.

Examination Report for Australian Application No. 2006314072, dated Jul. 5, 2011, 2 pages.

Office Action for Canadian Application No. 2,632,196, dated Mar. 16, 2010, 4 pages.

Supplementary European Search Report for European Application No. 06821561.5, dated Dec. 16, 2013.

Patent Examination Report No. 1 for Australian Application No. 2013260668, dated Jan. 4, 2016, 4 pages.

Office Action for U.S. Appl. No. 11/380,430 dated Mar. 5, 2009.

Office Action for U.S. Appl. No. 11/380,430, dated Nov. 13, 2009, 8 pages.

Office Action for U.S. Appl. No. 11/380,430, dated Mar. 24, 2010, 12 pages.

Office Action for U.S. Appl. No. 11/380,430, dated Sep. 1, 2010, 11 pages.

Office Action for U.S. Appl. No. 11/380,430, dated Oct. 29, 2010.

Office Action for U.S. Appl. No. 11/552,997 dated Mar. 24, 2009.

Office Action for U.S. Appl. No. 11/552,997 dated Oct. 30, 2007.

Office Action for U.S. Appl. No. 11/552,997 dated Aug. 5, 2008.

International Search Report for PCT/IL06/01326, dated Oct. 13, 2009.

Office Action for Australian Patent Application No. AU 2007245258, dated Apr. 12, 2012.

Office Action for Canadian Application No. 2,649,663, dated Nov. 20, 2013, 3 pages.

Office Action for Canadian Application No. 2,649,663, dated Oct. 28, 2014, 3 pages.

Supplementary European Search Report for European Application No. 07736271.3, dated Mar. 18, 2010.

Examination Report for European Application No. 07736271.3, dated Dec. 14, 2010.

Examination Report for European Application No. 07736271.3, dated Nov. 14, 2011.

Notice of Reasons for Rejection for Japanese Patent Application No. 2009-517597, dated Jan. 23, 2012.

Notice of Reasons for Rejection for Japanese Patent Application No. 2009-517597, dated Nov. 2, 2012.

Office Action for U.S. Appl. No. 12/299,043, dated Oct. 18, 2012.

Office Action for U.S. Appl. No. 12/299,043, dated Jul. 5, 2013.

International Preliminary Report on Patentability for PCT/IL07/00531, dated Mar. 10, 2009.

International Search Report for PCT/IL07/00531, dated Jul. 7, 2008.

European Search Report for European Application No. 12197261.6, dated Mar. 28, 2013.

Office Action for Japanese Application No. 2013-149122, dated May 19, 2014.

Office Action for U.S. Appl. No. 12/631,095, dated Sep. 14, 2011.

Office Action for U.S. Appl. No. 12/631,095, dated Apr. 17, 2012.

Office Action for U.S. Appl. No. 13/036,256, dated Apr. 5, 2012, 8 pages.

Office Action for U.S. Appl. No. 13/532,597, dated Apr. 23, 2013.

Office Action for U.S. Appl. No. 14/245,597, dated Dec. 16, 2015, 13 pages.

(56) References Cited

OTHER PUBLICATIONS

Office Action for U.S. Appl. No. 14/245,597, dated Jun. 24, 2016, 12 pages.
Office Action for U.S. Appl. No. 14/333,184, dated Jun. 18, 2015.
Office Action for U.S. Appl. No. 14/333,184, dated Oct. 28, 2015, 7 pages.
Office Action for U.S. Appl. No. 14/636,628, dated Sep. 20, 2016, 12 pages.
Office Action for U.S. Appl. No. 10/335,905, dated Jun. 11, 2009.
Office Action for U.S. Appl. No. 10/335,905, dated Apr. 18, 2008.
Office Action for U.S. Appl. No. 10/335,905, dated Dec. 19, 2005.
Office Action for U.S. Appl. No. 10/335,905, dated Apr. 2, 2010.
Office Action for U.S. Appl. No. 10/335,905, dated Jan. 30, 2007.
Office Action for U.S. Appl. No. 10/335,905, dated Dec. 24, 2008.
Office Action for U.S. Appl. No. 10/335,905, dated Jan. 14, 2011.
Supplementary European Search Report and Opinion for European Application No. 15770404.0, dated Oct. 19, 2017, 8 pages.
Office Action for U.S. Appl. No. 14/223,340, dated Oct. 21, 2015, 7 pages.
Office Action for U.S. Appl. No. 14/223,340, dated Jun. 16, 2016, 10 pages.
Office Action for U.S. Appl. No. 14/223,340, dated Jan. 11, 2017, 9 pages.
International Search Report and Written Opinion for International Application No. PCT/US2015/020992, dated Jun. 24, 2015.
International Search Report and Written Opinion for International Application No. PCT/US2017/012977, dated Mar. 17, 2017, 12 pages.
Alon, G. et al., "Persons with C5 or C6 tetraplegia achieve selected functional gains using a neuroprosthesis," Arch. Phys. Med. Rehabil., 84:119-124 (Jan. 2003).
Bajd, et al., "Funcational Electrical Stimulation: standing and walking after spinal cord injury," CRC Press, Boca Raton, Florida, 1989 (Table of Contents).
Bogataj, U. et al., "Preliminary testing of a dual-channel electrical stimulator for correction of gait," Journal of Rehabilitation Research and Development, vol. 24, No. 3, pp. 75-80, Summer 1987. Retrieved from the Internet: Dec. 29, 2016, <URL: http://www.rehab.research.va.gov/jour/87/24/3/pdf/bogataj.pdf>.
Burridge, et al., "Two-channel stimulation for hemiplegic gait. Control Algorithms, selection of muscle groups and the result of preliminary clinical trial," 6th Internet World Congress for Biomedical Sciences, INABIS 2000.
"Clinical evaluation of the ljubljana functional electrical peroneal brace," Subcommittee on Evaluation, Committee on Prosthetics Research and Development Division of Medical Sciences—National Research Council, National Academy of Sciences, Washington, D.C., Report E-7 (1973).
Daly, W. K., "Electrodes installed in roll-on suspension sleeves," From "MEC '02 The Next Generation," Proceedings of the 2002 MyoElectric Controls/Powered Prosthetics Symposium, Fredericton, New Brunswick, Canada: Aug. 21-23, 2002, University of New Brunswick, 3 pages.
Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).
Doucet, B. M. et al., "Neuromuscular Electrical Stimulation for Skeletal Muscle Function," Yale Journal of Biology and Medicine, 85:201-215 (2012).
Duncan, R. M., "Basic principles of splinting the hand," Journal of the American Physical Therapy Association, 69(12):1104-1116 (1989).
Hart, R. L. et al., "A comparison between control methods for implanted FES hand-grasp systems," IEEE Transactions on Rehabilitation Engineering, 6(2):208-218 (Jun. 1998).
Hendricks, H. T. et al., "Functional electrical stimulation by means of the 'Ness Handmaster Orthosis' in chronic stroke patients: an exploratory study," Clinical Rehabilitation, 15:217-220 (2001).

Kralj, A. et al., "Functional electrical stimulation of the extremities: part 1," Journal of Medical Engineering and Technology, pp. 12-15 (Jan. 1977).
Kralj, A. et al., "Functional electrical stimulation of the extremities: part 2," Journal of Medical Engineering and Technology, pp. 75-80 (Mar. 1977).
Kralj, A. R. et al., "Functional Electrical Stimulation: Standing and Walking after Spinal Cord Injury," CRC Press, Boca Raton, FL., pp. 1-15 (1989).
Liberson, W. T. et al., "Functional Electrotherapy: Stimulation of the Peroneal Nerve Synchronized with the Swing Phase of the Gait of Hemiplegic Patients," 3rd International Congress of Physical Medicine, Session on Neuromuscular Diseases, Washington DC, Aug. 25, 1960, pp. 101-105.
Liberson, W. T. et al., "Functional Electrotherapy: Stimulation of the Peroneal Nerve Synchronized with the Swing Phase of the Gait of Hemiplegic Patients," Archives of Physical Medicine & Rehabilitation, pp. 101-105 (Feb. 1961).
NDI Medical, "About ODFS Dropped Foot Stimulator," [online] 2005 [retrieved on Jun. 5, 2006]. Retrieved from the Internet: URL: <http://www.odfs.com/About_ODFS/about_odfs.html>.
NESS H200 Product Specifications "H200™ Overview& Product Specifications," [online] 2006 [retrieved on Jun. 5, 2007]. Retrieved from the Internet: URL: <http://www.bionessinc.com/products/h200/htm>.
Neurodan, "ActiGait® An implantable drop foot correction system," Neurodan A/S—Products—ActiGait® [online] [retrieved on Jun. 5, 2007]. Retrieved from the Internet: URL: <http://www.neurodan.com/actigait.asp>.
NMES Guidelines for Treatment "Gait Training," [online] [retrieved on May 30, 2007]. Retrieved from the Internet: URL: <http://www.empi.com/products1nmes/gait.pdf>.
Popovic, M. R. et al., "Neuroprostheses for grasping," Neurological Research, 24:443-452 (Jul. 2002).
Popovic, M. R. et al., "Functional electrical therapy: retraining grasping in spinal cord injury," Spinal Cord, 44:143-151 (2006).
Popovic, et al., "Functional Electrical Stimulation for Grasping and Walking: Indications and Limitations," Spinal Cord, (Jun. 2001), 22 pages.
Popovic, et al., "Surface Stimulation Technology for Grasping and Walking Neuroprostheses—Improving Quality of Life in Stroke/Spinal Cord Injury Subjects with Rapid Prototyping and Portable FES Systems," IEEE Engineering in Medicine and Biology, Jan./Feb. 2001.
Prochazka, A. et al., "The bionic glove: An electrical stimulator garment that provides controlled grasp and hand opening in quadriplegia," Arch. Phys. Med. Rehabil., 78:608-614 (Jun. 1997).
Senelick, R. C., "Technological Advances in Stroke Rehabilitation-High Tech Marries High Touch," US Neurology, 6(2):102-104 (2010), Extract (Touch Group PLC, 4 pages).
Shenzhen XFT Electronics Co., Ltd., Foot Drop System, XFT-2001 User Manual, 16 pages. Retrieved from the Internet: Aug. 10, 2016, <URL: http://www.stressnomore.co.uk/downloads/instructions/91846-IFUS_1.pdf>.
Sowerbutt, C., "Restoring Gait in Stroke Patients Using Functional Neuromuscular Stimulation," [online] Sep. 1, 2006 [retrieved on May 30, 2007]. Retrieved from the Internet: URL: <http://appneurology.com/showArticle.jhtml?print=true&articleID=193104432>.
Springer, S. et al., "Dual-channel functional electrical stimulation improvements in speed-based gait classifications," Clinical Interventions in Aging, 8:271-277 (2013).
Springer, S. et al., "The effects of dual-channel functional electrical stimulation on stance phase sagittal kinematics in patients with hemiparesis," Journal of Electromyography and Kinesiology (2012), 7 pages, http://dx.doi.org/10.1016/j.jelekin.2012.10.017.
Stanic, U., "History of functional electrical stimulation," International Functional Electrical Stimulation Society, INS & IFESS Joint Congress, Sep. 16-20, 1998, Lucerne, Switzerland, 37 pages.
Stopar, M. et al., "New stimulators for cutaneous stimulation," Advances in External Control of Human Extremities, Proceedings of the Seventh International Symposium on External Control of Human Extremities, pp. 267-272 (1981).

(56) References Cited

OTHER PUBLICATIONS

Stralka, "Gait Training (by Stimulating Dorsiflexors)," NM III™ Neuromuscular Stimulation System Suggested Protocol, NM III Program Set #2 Program F, Rehabilicare® 920080 Rev. C.

Strojnik, P. et al., "Treatment of drop foot using an implantable peroneal underknee stimulator," Scandanavian J. of Rehabil. Med. 19:37-43 (1987).

Strojnik, P. et al., "Implantable stimulators for neuromuscular control," Chapter 78 in The Biomedical Engineering Handbook: Second Edition, Bronzino, J. D. (ed.), Boca Raton: CRC Press LLC (2000), 15 pages.

Uellendahl, J. E. et al., "Custom silicone sockets for myoelectric prostheses," Journal of Prosthetics and Orthotics, 18(2):35-40 (2006).

Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.

Vodovnik, L. et al., "Functional electrical stimulation for control of locomotor systems," CRC Critical Reviews in Bioengineering, 6(2):63-131 (Sep. 1981).

Ward, A. R. et al., "Russian electrical stimulation: The early experiments," Physical Therapy, 82(10):1019-1030 (Oct. 2002).

Waters, R. L. et al., "Effectiveness of selected surface electrodes for motor stimulation," Advances in External Control of Human Extremities, Proceedings of the Sixth International Symposium on External Control of Human Extremities, pp. 31-38 (1978).

Waters, R. L. et al., "Experimental correction of footdrop by electrical stimulation of the peroneal nerve," J Bone Joint Surg Am., vol. 38, No. 8 (Dec. 1975), pp. 1047-1054.

Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.

Wood, D.E., "Spatial sensitivity comparisons between an implanted and surface dropped foot neuromuscular stimulator," 9th Annual Conference of the International FES Society, Sep. 2004.

European Office Action for European Application No. 15770404.0, dated Oct. 8, 2019, 5 pages.

Home Medical Supplies and Equipments XFT, "The Latest G3 Foot Drop System, XFT-2001" accessed Mar. 2, 2015, 3 pages, retrieved from http://www.xft-china.com/product/detail_62_The_Latest_Foot_Drop_System.html.

Innovative Neurotronics, "How WalkAide Works," accessed Mar. 2, 2015, 1 page, retrieved from http://www.walkaide.com/patients/Pages/HowWalkAideWorks.aspx.

Innovative Neurotronics, "WalkAide as Rehabilitation Tool, The New WalkAide System: The Dynamic FES for Neuro Rehabilitation," accessed Mar. 2, 2015, 4 pages, retrieved from http://www.walkaide.com/medicalprofessionals/Pages/WalkAideforRehab.aspx.

Odstock Medical Ltd, Datasheet for ODFS QF/120/Pace v1.0, accessed Sep. 12, 2019, 1 page, retrieved from https://www.odstockmedical.com/sites/default/files/datasheet_for_odfs_pace_v1.0_qf120_doc_iss6_web.pdf.

Odstock Medical Ltd, Product Data Sheet for ODFS Leg Cuff V1.0, accessed Sep. 12, 2019, 2 pages, retrieved from https://www.odstockmedical.com/sites/default/files/product_data_sheet_-_leg_cuff_v1.0.pdf.

Odstock Medical Ltd, "Walking," accessed Sep. 12, 2019, 2 pages, retrieved from https://www.odstockmedical.com/walking.

SYSTEMS AND APPARATUS FOR GAIT MODULATION AND METHODS OF USE

CROSS-REFERENCE TO RELATED PATENT APPLICATIONS

This application is a continuation of U.S. patent application Ser. No. 15/872,634 (now U.S. Pat. No. 10,086,196), filed on Jan. 16, 2018, entitled "Systems and Apparatus for Gait Modulation and Methods of Use," which is a division of U.S. patent application Ser. No. 14/223,340 (now U.S. Pat. No. 9,867,985), filed on Mar. 24, 2014, entitled "Systems and Apparatus for Gait Modulation and Methods of Use," the disclosure of each of which is incorporated herein by reference in its entirety.

BACKGROUND

The embodiments described herein relate generally to gait modulation systems, and more particularly, to a functional electrical stimulation (FES) orthosis for gait modulation and methods of using the same.

It is known that pathologies of the neuromuscular system due to disease or trauma to the central nervous system, such as for example, stroke, spinal cord injury, head injury, cerebral palsy, and multiple sclerosis can impede limb function of the arms or legs (or portions thereof). Gait, the biomechanical description of walking, can suffer static and dynamic parameter variations due to neuromuscular impairments, which cause non-symmetrical walking, reduced walking speed, and reduced walking stability. For example, drop foot describes a gait attributable to weak or uncoordinated activation of the ankle dorsiflexors due to disease or trauma to the central nervous system. Patients suffering from drop foot tend to drag the foot during the swing phase of walking and usually try to compensate for this dragging by hiking the corresponding hip or swinging the corresponding leg in a circular motion. These patients tend to have reduced stability, are prone to frequent falls, and their walking movements are unaesthetic and energy consuming.

Limb muscles, however, can generally be activated with functional electrical stimulation (FES). In FES, precisely timed bursts of short electrical pulses (e.g., from a neuroprosthetic, an FES orthosis, and/or the like) are applied to motor nerves to generate muscle contraction, which can be applied to enhancing limb function. Although neuroprosthetic systems are known, some such systems suffer from drawbacks that prevent the systems from being widely used by potential patients. For example, in instances in which stroke or brain injury results in problems with arm movement or gait, such problems are often accompanied by hand impairment on the same side of the body as the problematic limb. Thus, donning an FES orthosis is often carried out using solely the contra-lateral, unaffected hand. Moreover, the posture of the plegic limb is often problematic, especially in cases where spasticity results in reduced voluntary movements and/or limited passive range of motion of the limb joints. Consequently, objective biomechanical problems exist in donning some known orthotic devices as well as locating the electrodes in exact positions onto the limb, which is essential for activating the desired movement pattern. As such, some known neuroprosthetic devices fail to enable facile, quick, and accurate donning of the device by an impaired patient using a single hand, and particularly, when the least effected hand is shaky or otherwise unstable.

FES devices typically utilize a stimulator unit to create and control the electrical pulses being applied to motor nerves that is physically separate from the FES orthosis. The external stimulator unit, which is connected to the FES orthosis by several electrical wires, is located on the body of the user and/or is otherwise worn by the user. These devices can be inconvenient for the user. Specifically, the wiring, which is usually arranged to run along the leg under the clothing to connect the device components, can be difficult to operate, cumbersome and uncomfortable.

In other instances, an FES orthosis can be a self-contained device. For example, some known orthoses can include a stimulator unit coupled to a narrow band that is made of a thermoplastic material, which is molded to the limb anatomy of an individual user by heating and softening the thermoplastic material and subsequently fitting the band to the contour of the underlying limb segment. Thus, the shape and size of the device and the electrode positioning is custom-fitted to the leg of one user and individualized for the user. This procedure is carried out by a medical professional trained, for example, to accurately identify the stimulation points that cause contraction of the muscles, positioning and locking the electrodes thereto.

Activation of the leg muscles by electrical stimulation typically includes transferring high stimulation currents through one or more electrodes to the skin surface of the patient, which activates skin sensory receptors in addition to underlying excitable motor nerve and muscle tissue. As a result, the intensity of sensory activation often depends on the intensity of the current density passing through the skin surface. The level of muscle activation, therefore, is often limited to the patient's individual tolerance to activation of such skin pain sensors. Thus, the stimulation parameters of the device are adjusted for each patient, which can be time consuming and often includes attaching the orthosis to a control device via wires.

Therefore, a need exists for improved systems and apparatus for a neuroprosthetic system that can be easily and accurately donned on the limb by patient and that includes a stimulation unit that can be remotely controlled and/or adjusted.

SUMMARY

Systems and apparatus for gait modulation and methods of use are described herein. In some embodiments, an apparatus includes a frame assembly, a sensor, and an electric stimulator. The frame is configured to be removably coupled to a portion of a limb such that the portion of the limb is substantially enveloped by the frame. The sensor is operably coupled to the frame and is configured to produce a first signal associated with a gait characteristic at a first time, and a second signal associated with the gait characteristic at a second time, after the first time. The first time and the second time define a time period therebetween. The electric stimulator is removably coupled to the frame and is in electrical communication with the sensor and an electrode assembly. The electrode assembly is in electrical communication with a portion of a neuromuscular system of the limb when the frame is coupled thereto and is configured to receive the first signal from the sensor substantially at the first time and the second signal from the sensor substantially at the second time. Based at least in part on the gait characteristic at the first time, the electric stimulator is configured to send a third signal to the electrode assembly substantially at the first time operable to cause the electrode assembly to provide an electric stimulation to the portion of the neuromuscular system of the limb substantially during the time period.

DETAILED DESCRIPTION

Figure 1:
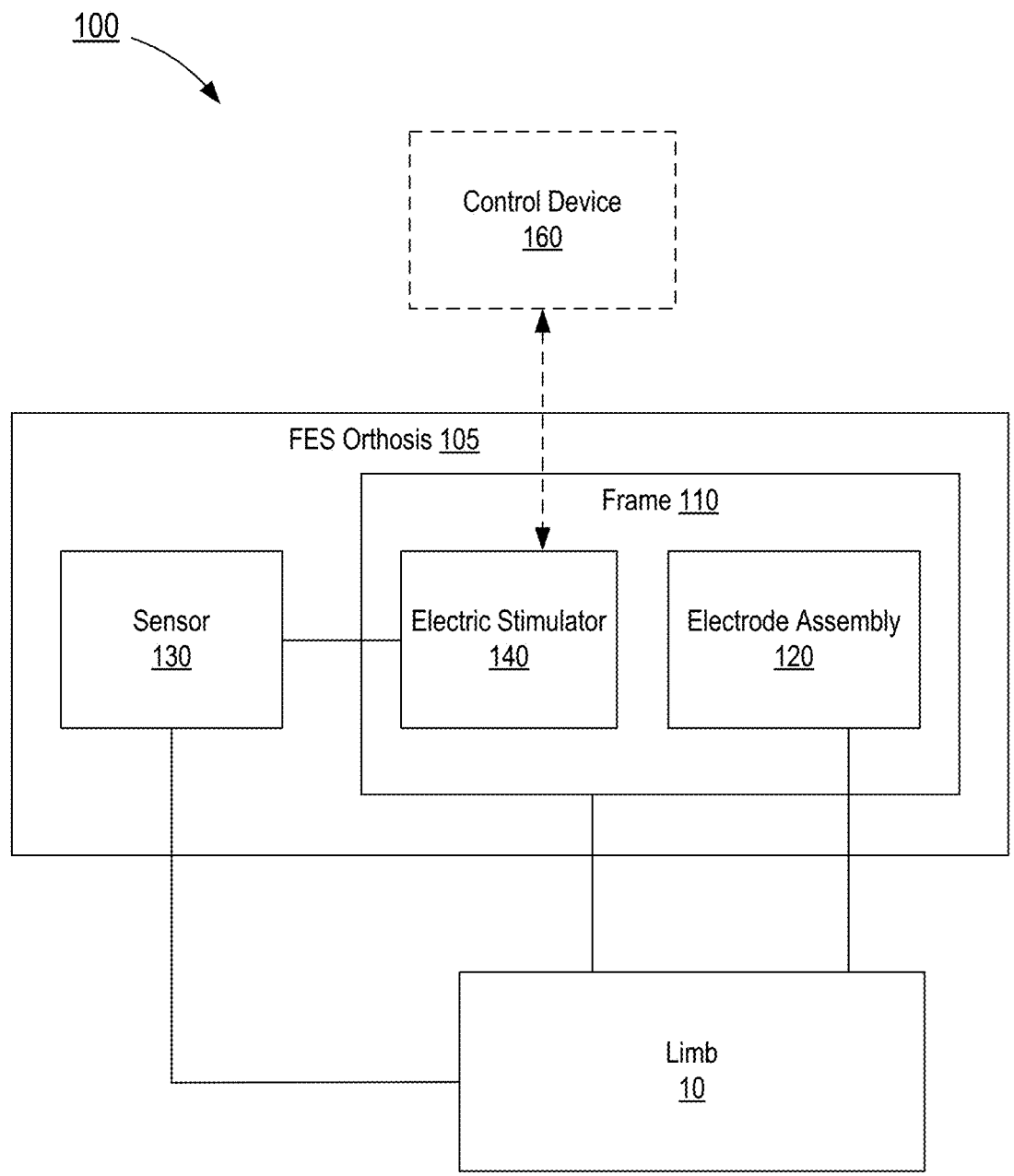
FIG. 1 is a schematic illustration of a system for gait modulation according to an embodiment.

The embodiments and methods described herein relate to an improved functional electrical stimulation (FES) orthosis for users suffering from gait problems such as drop foot. The orthosis can easily be donned on the leg, even by patients suffering from impairments that might otherwise hinder the donning of the orthosis. In some embodiments, an apparatus includes a frame assembly, a sensor, and an electric stimulator. The frame is configured to be removably coupled to a portion of a limb such that the portion of the limb is substantially enveloped by the frame. The sensor is operably coupled to the frame and is configured to produce at least a first signal associated with a gait characteristic at a first time, and a second signal associated with the gait characteristic at a second time, after the first time. The first time and the second time define a time period therebetween. The electric stimulator is removably coupled to the frame and is in electrical communication with the sensor and an electrode assembly. The electrode assembly is in electrical communication with a portion of a neuromuscular system of the limb when the frame is coupled thereto and is configured to receive the first signal from the sensor substantially at the first time and the second signal from the sensor substantially at the second time. Based at least in part on the gait characteristic at the first time, the electric stimulator is configured to send a third signal to the electrode assembly substantially at the first time operable to cause the electrode assembly to provide an electric stimulation to the portion of the neuromuscular system of the limb substantially during the time period.

In some embodiments, a method includes receiving, at an electric stimulator and from a sensor, a first signal associated with a gait characteristic. Based at least in part on the first signal associated with the gait characteristic, one or more system parameters is calculated. A signal is sent, based at least in part on the one or more system parameters, from the electric stimulator to an electrode assembly to cause the electrode assembly to provide an electric stimulation to a portion of a neuromuscular system of a limb. A second signal associated with the gait characteristic is received at the electric stimulator from the sensor. The method includes terminating the electric stimulation of the portion of the neuromuscular system of the limb based on receiving the second signal associated with the gait characteristic.

In some embodiments, a method of using an electric stimulator having a sensor and an electrode assembly in electrical communication with a portion of a neuromuscular system of a limb includes receiving, at the electric stimulator, a first signal that is sent from a control device via a first communication channel associated with a wireless communication over a network. The first signal is associated with a system parameter. A second signal is sent from the electric stimulator to the control device via the first communication channel. The second signal is associated with a confirmation of the system parameter. The electric stimulator receives a third signal that is sent from the sensor via a second communication channel, different from the first communication channel. The third signal is associated with a gait characteristic. The method includes sending, from the electric stimulator to the electrode assembly, a fourth signal. The fourth signal is operable to cause the electrode assembly to provide an electric stimulation to the portion of the neuromuscular system of the limb based at least in part on the system parameter and the gait characteristic.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "limb segment" refers to at least a portion of a mammalian appendage. For example, the embodiments described herein can be coupled to and/or otherwise placed in contact with a limb segment that can include a portion of the upper and/or lower arm, or a portion of the upper and/or lower leg of a human body.

As used herein, the terms "envelop," "enveloping," and/or the like, with regard to a limb segment and an article or device coupled thereto, refer to an article or device that substantially surrounds and/or covers at least one half the circumference of a limb segment when coupled thereto. For example, if when coupled to a limb segment, an article or device substantially circumscribes a portion of the limb segment, the article or device can be said to envelop the portion of the limb segment.

As used herein, the terms "FES orthosis," "orthosis," "neuroprosthetic," "FES device," "device," and/or the like can be used interchangeably and refer generally to a medical apparatus that is selectively placed in contact with a portion of a patient. As described herein, such devices can include one or more electrodes that can transmit a flow of electrical current to a portion of a neuromuscular system associated with the portion of the patient, thereby providing functional electrical stimulation to, for example, an impaired limb.

As used herein, the terms "reversible," "reversibly," and/or the like when used to described a process and/or procedure generally refer to a non-destructive process or procedure that can be subsequently undone by a similar yet substantially opposed, inverse, and/or opposite non-destructive process or procedure. When used herein with respect to attachment and/or detachment of an element or assembly, a reversible attachment refers to a non-destructive, repeatable attachment and/or detachment of the element or assembly.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the terms "about" and "approximately" generally mean plus or minus 10% of the value stated, unless the context clearly expresses otherwise. For example, about 0.5 would include 0.45 and 0.55, about 10 would include 9 to 11, about 1000 would include 900 to 1100. In some instances, such as when assessing a gait phase of a stimulation parameter and/or the like, the terms about and approximately can generally mean greater than plus or minus 10% of the value stated.

As used herein, the terms "communication channel," "communication mode," and/or "modality" can be used interchangeably and refer generally to one or more modes of communication using, for example, one or more electronic devices. Such modes of communication can be associated with a specific format (e.g., a data unit format) that, in some instances, can be unique to that mode of communication (e.g., a different protocol, a different data unit structure or arrangement, etc.). For example, a cellular telephone (e.g., a smart phone) can send a communication to another electronic device such as an electric stimulator via a modality and/or via a network that is associated with the cellular telephone (e.g., a short message service (SMS) modality, a multimedia message service (MMS) modality, a Bluetooth® modality, a wireless fidelity (WiFi®) modality, etc.). Thus, when referring to a channel and/or modality, the channel and/or modality includes, defines, and/or otherwise is associated with a data unit format suitable for transmission of data via that communication mode.

As used herein, the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based modules (e.g., a field-programmable gate array (FPGA), an application specific integrated circuit (ASIC), a digital signal processor (DSP)) and/or software-based modules (e.g., a module of computer code stored in memory and/or executed at the processor) capable of performing one or more specific functions associated with that module.

FIG. 1 is a schematic illustration of a system 100 used for gait modulation according to an embodiment. For example, in some instances, the system 100 can be used by a human patient who has one or more impaired limbs as a result of injury and/or disease (e.g., stroke, spinal cord injury, head injury, cerebral palsy, multiple sclerosis, etc.). More specifically, the system 100 includes a functional electrical stimulation (FES) orthosis 105 (also referred to herein as "orthosis" and/or "device") that is placed in physical and electrical contact with a limb 10 of the patient such as, for example, a lower limb segment of an impaired leg. As such, the patient and/or a health care professional (e.g., doctor, nurse, technician, physician, physical therapist, etc.) can engage the system 100 in such a manner as to cause the orthosis 105 to selectively provide electrical stimulation to a portion of a neuromuscular system of the limb 10, which can, in turn, facilitate gait of the patient who might otherwise experience, for example, drop foot or the like, as described in further detail herein.

The orthosis 105 includes a frame 110, an electrode assembly 120, one or more sensors 130, and an electrical stimulator 140. In some embodiments, at least a portion of the orthosis 105 can be substantially similar in form and function as those described in U.S. Pat. No. 7,899,556 entitled, "Gait Modulation System and Method," filed Apr. 27, 2006 (referred to henceforth as the "'556 patent"), U.S. Pat. No. 8,209,036 entitled, "Gait Modulation System and Method," filed Nov. 12, 2006 (referred to henceforth as the "'036 patent"), and U.S. patent application Ser. No. 13/532,597 entitled, "Gait Modulation System and Method," filed Jun. 25, 2012 (referred to henceforth as the "'597 application"), the disclosures of which are incorporated herein by reference in their entireties.

At least a portion of the frame 110 can be formed from a semi-rigid material such as, for example, a relatively thin metal, a thermoplastic, a polymer, and/or the like, which can enable the frame 110 to provide structural support for the orthosis 105. The frame 110 can have any suitable shape and/or size that can be, for example, associated with a segment of the limb 10 (e.g., a lower segment of a patient's leg). Moreover, at least a portion of the frame 110 can be transitioned between a first configuration and a second configuration to couple the frame 110 to the limb 10. For example, in some embodiments, the frame 110 can include a coupling portion or the like that can be transitioned between a first (e.g., open) configuration and a second (e.g., closed) configuration to at least temporarily couple the frame 110 to the limb 10. Expanding further, when the orthosis 105 is coupled to the limb 10, the frame 110 can be configured to substantially envelop and/or circumscribe the limb 10. In some embodiments, the coupling portion can be one or more straps, clips, ratchets, and/or the like that can allow for facile placement and coupling to the frame 110 to the limb 10, as described in further detail herein.

The electrode assembly 120 of the orthosis 105 is coupled to an inner surface of the frame 110. As such, when the frame 110 is coupled to the limb 10 (e.g., transitioned from its first configuration to its second configuration), at least a portion of the electrode assembly 120 is placed in contact with a surface of the limb 10, as described in further detail herein. The electrode assembly 120 can be any suitable arrangement of hardware and/or software. For example, in some embodiments, the electrode assembly 120 can include one or more electrodes that are each electrically coupled to a wire, electrical trace, and/or the like that are operable in electrically coupling the one or more electrodes to the electric stimulator 140. In some embodiments, at least a portion of the electrode assembly 120 can be disposed within a portion of the frame 110. For example, in such embodiments, the electrode assembly can include a set of wires that are substantially enclosed by a portion of the frame 110. The wires can include end portions that each include a connector or the like that can, for example, be electrically coupled to the electric stimulator 140 at a first end portion and that can, for example, be electrically coupled to the electrodes at a second end portion. In some embodiments, the electrode assembly 120 can be substantially similar in form and function as those described in the '556 patent, the '036 patent, and/or the '597 application.

The sensor 130 of the orthosis 105 can be any suitable sensor device or can include a combination of sensor devices. For example, in some embodiments, the sensor 130 can include a tilt sensor, an accelerometer, a gyroscope, a pressure sensor, a speedometer, and/or the like. In this manner, when the system 100 is used for gait modulation of a patient with an impaired limb (i.e., leg), the sensor 130 can be configured to sense and/or otherwise detect a characteristic associated with, for example, a gait event such as position of the sensor 130 relative to the orthosis 105, position of the limb 10 relative to a reference plane or the like, angular position of the limb 10 relative to a reference plane or the like, velocity, rate of change in velocity (i.e., acceleration), tilt of the patient's foot, pressure (e.g., when the foot and/or shoe contacts a surface upon which the patient is walking), etc.

In some embodiments, the sensor 130 can be included in and/or integrated with the frame 110, the electrode assembly 120, and/or the electric stimulator 140. In other embodiments, the sensor 130 can be physically distinct from the orthosis 105 and in electrical communication with the electric stimulator 140 via a wireless communication channel. For example, in some embodiments, the electric stimulator 140 can be coupled to the frame 110, which in turn, is coupled to a first segment of the limb (e.g., adjacent to the knee of the patient's leg) and the sensor 130 can be coupled to and/or otherwise can be associated with a second segment of the limb 10 (e.g., adjacent to the foot and/or ankle of the patient's impaired leg). In some embodiments, the sensor 130 can be coupled and/or otherwise can be associated with a segment of the contralateral leg (e.g., adjacent to the foot and/or ankle of the patient's leg not donning the electric stimulator 140). In some embodiments, the system 100 can include multiple distinct sensors 130. For example, in some embodiments, the system 100 can include a first sensor that is integrated with the electric stimulator 140 and a second sensor that is physically distinct from, yet in electrical communication with, the electric stimulator 140 (e.g., disposed within and/or coupled to a shoe of the patient). In such embodiments, the electrical stimulator 140 can be configured to receive signals from and/or send signals to the first sensor via a first communication channel, associated with a wired signal transmission (e.g., signals transmitted along a wire or signal trace), and a second communication channel, associated with a wireless signal transmission (e.g., WiFi®, Bluetooth®, etc.), as described in further detail herein.

The electric stimulator 140 of the orthosis 105 can be any suitable functional electrical stimulation device having any combination of hardware and software. For example, the electric stimulator 140 can be an electronic device that can include one or more electrical circuits operable in providing a flow of electrical current to at least a portion of the neuromuscular system of the limb 10. The electric stimulator 140 of the orthosis 105 is removably coupled to the frame 110. For example, in some embodiments, the frame 110 can form a cradle and/or the like that can be configured to at least temporarily retain the electrical stimulator 140 therein, as described below with respect to specific embodiments. Moreover, the electric stimulator 140 is configured to be placed in electrical communication with the electrode assembly 120 and the sensor 130. In some embodiments, the electrode assembly 120 and/or the sensor 130 can be included in (e.g., integrated with) the electric stimulator 140. In other embodiments, the electrode assembly 120 and the sensor 130 can be operably coupled to the electric stimulator 140 via any suitable wiring, connector, interface, and/or structure. For example, in some embodiments, the frame 110 can include a connector and/or the like configured to place the electric stimulator 140 in electrical communication with, for example, the electrode assembly 120 and/or the sensor 130.

In some embodiments, the electric stimulator 140 can receive and/or send signals to a set of external and/or implanted electrical devices via any suitable communication mode. For example, in some embodiments, the electric stimulator 140 can include two, three, four, five, six, or more communication and/or electrical channels that can be operable in sending and/or receiving signals to and/or from, respectively, the electrode assembly 120, the sensor 130, and/or any other suitable electronic device operably coupled thereto. In some embodiments, at least a portion of the communication and/or electrical channels can be associated with sending and/or receiving signal via a wireless communication modality (e.g., a modality, format, and/or the like associated with WiFi®, Bluetooth®, near field communication (NFC), cellular communication such as, short message service (SMS) or multimedia message service (MMS), and/or the like), as described in further detail herein.

As described above, in some instances, the system 100 can be used for gait modulation of patients with an impaired limb. More specifically, the system 100 can be used to enhance the limb function of a patient experiencing drop foot. In such instances, the patient can manipulate the orthosis 105 in such a manner as to couple the orthosis 105 to the impaired limb. For example, the patient can position the orthosis 105 adjacent to the knee of an impaired leg and can transition the frame 110 from a first configuration to a second configuration (as described above) to removably couple the orthosis 105 to the leg. The placement of the orthosis 105 can be such that a set of electrodes included in the electrode assembly 120 are disposed in a location relative to the leg that is associated and/or corresponds to a desired portion of the neuromuscular system of the leg. More specifically, to enhance the leg function of a patient experiencing drop foot during gait, the orthosis 105 can be positioned relative to the leg to place the electrodes in electric communication with the peroneal nerve and/or the tibial nerve. Thus, the electrodes can transmit functional electrical stimulation to the peroneal nerve, which can result in dorsiflexion of the foot, and/or the tibial nerve, which can result in plantarflexion of the foot, thereby enhancing the function of the impaired leg to mitigate the effects of drop foot, as described in further detail herein.

With the frame 110 retained in the desired position relative to the impaired leg, the patient can begin walking. During walking, the sensor 130 can be configured to sense and/or detect a set of characteristics (such as those described above) associated with a gait event and can send a signal associated with the characteristic to the electric stimulator 140. For example, in some embodiments, the gait event can be associated with a "heel-off" event (i.e., the point during gait at which the heel is lifted off the surface upon which the patient is walking). The sensor 130 can send the signal to the electric stimulator 140 via any suitable communication channel. For example, if the sensor 130 is collocated with at least a portion of the electric stimulator 140 and/or the frame 110, the sensor 130 can send the signal via a communication channel associated with a wired signal transmission. If, however, the sensor 130 is physically distinct from the other portions of the orthosis 105, the sensor can send the signal via a communication channel associated with a wireless signal transmission, such as those described above. In some embodiments, the electric stimulator 140 can receive a signal from multiple sensors 130 that can be configured to sense and/or detect a characteristic associated with a gait event at different segments along the leg of the patient.

Upon receiving the signal from the sensor 130, the electric stimulator 140 can be configured to transmit an electrical current resulting from a relatively high voltage (e.g., generated by a power supply or the like included in the electric stimulator 140) along an electric circuit that is electrically coupled to the electrode assembly 120. Thus, the current resulting from the relatively high voltage (also referred to herein as "high current") is transmitted to the electrodes of the electrode assembly 120, which in turn, provide FES to the peroneal nerve, thereby resulting in dorsiflexion and/or plantarflexion of the foot substantially at the time of the heel-off event (e.g., a very short time after the sensor 130 detects the heel-off event consistent with a rate of electrical signal and/or electrical current transmission such as, 0.10 seconds, 0.05 seconds, 0.01 seconds, 0.001 seconds, 0.0001 seconds, or less). As a result, the foot of the patient flexes toward the leg, enhancing a portion of the patient's gait.

In some instances, the sensor 130 can sense and/or detect a characteristic associated with a second gait event such as, for example, a "heel-on" event (i.e., the point during gait at which the heel is placed in contact with the surface of upon which the patient is walking). As described above, the sensor 130 can send a signal associated with the characteristic to the electric stimulator 140 and, upon receipt, the electric stimulator 140 can terminate the flow of the relatively high current to the electrodes in electrical contact with the peroneal nerve. In some instances and in a substantially concurrent process, the electric stimulator 140 can generate a relatively high current along an electric circuit that is electrically coupled to one or more electrodes in electrical communication with the tibial nerve. Thus, the electrodes can provide FES to the tibial nerve resulting in plantarflexion of the foot substantially at the time of the heel-on event (as described above). In this manner, the termination of the FES to the peroneal nerve relaxes the portion of the neuromuscular system resulting in a relaxation of the dorsiflexion, while substantially concurrently, the FES provided to the tibial nerve results in plantarflexion of the foot. As such, the foot flexes away from the leg, enhancing a portion of the patient's gait.

In some embodiments, the electric stimulator 140 can include, for example, a memory or the like that can be configured to store information at least partially defining a set parameters associated with the FES. For example, in some embodiments, the electrical stimulator 140 can be configured to store information associated with a voltage and/or current level associated with the FES, a sensitivity associated with the sensor 130, a repository of actions to perform based on information received from the sensor 130, and/or any other suitable information and/or logic. Thus, the electric stimulator 140 can be configured to provide FES to the impaired leg with a set of characteristics that can be uniquely associated with the patient. In some instances, the patient and/or a health care professional can manipulate the electric stimulator 140 to change one or more parameters and/or characteristics associated with the FES provided to the impaired leg.

As shown in FIG. 1, in some embodiments, the electric stimulator 140 can be in communication with a control device 160. The control device 160 can be any suitable electronic device that can provide an interface for a user (e.g., the patient and/or a health care professional) to manipulate one or more characteristics and/or parameters associated with the FES. For example, in some embodiments, the control device 160 can be, for example, a personal computer (PC), a personal digital assistant (PDA), a smart phone, a laptop, a tablet PC, a server device, a workstation, and/or the like. The electronic device can include at least a memory (e.g., a random access memory (RAM), a memory buffer, a hard drive, a read-only memory (ROM), an erasable programmable read-only memory (EPROM), and/or the like); a processor (e.g., a general purpose processor, a central processing unit (CPU), an accelerated processing unit (APU), and Application Specific Integrated Circuit (ASIC), and/or the like); a network interface (e.g., a network interface card and/or the like that can include at least an Ethernet port and/or a wireless radio (e.g., a WiFi® radio, a Bluetooth® radio, etc.)); and an output device (e.g., a display such as a cathode ray tube (CRT) monitor, a liquid crystal display (LCD) monitor, a light emitting diode (LED) monitor, and/or the like, a Universal Serial Bus (USB) drive, an ANT+ compatible device or application, and/or any other suitable output device). In this manner, the control device 160 can be in communication with the electric stimulator 140 via the network interface and the processor can be configured to run or execute a set of instructions or code stored in the memory associated with using, for example, a PC application, a mobile application, an internet web browser, a cellular and/or wireless communication (via a network), and/or the like to communicate with and/or otherwise control at least a portion of the electric stimulator 140, as described herein with respect to specific embodiments.

FIGS. 2-8 are illustrations of a system 200 used, for example, in gait modulation according to an embodiment. For example, in some instances, the system 200 can be used by a human patient who has one or more impaired limbs as a result of injury and/or disease (e.g., stroke, spinal cord injury, head injury, cerebral palsy, multiple sclerosis, etc.). More specifically, the system 200 includes a functional electrical stimulation (FES) orthosis 205 (also referred to herein as "orthosis" and/or "device") that is placed in physical and electrical contact with, for example, a lower limb segment of an impaired leg 20 (see e.g., FIG. 4). In some embodiments, at least a portion of the orthosis 205 can be substantially similar in form and/or function to those described in the '556 patent, the '036 patent, and the '597 application incorporated by reference in their entireties above. As such, the patient and/or a health care professional (e.g., doctor, nurse, technician, physician, physical therapist, etc.) can engage the system 200 in such a manner as to cause the orthosis 205 to selectively provide functional electrical stimulation to a portion of a neuromuscular system of the leg 20, which can, in turn, facilitate gait of the patient who might otherwise experience, for example, drop foot or the like, as described in further detail herein.

As shown in FIGS. 2-7, the orthosis 205 includes a frame 210, an electrode assembly 220, and an electrical stimulator 240. Although not shown in FIGS. 2-7, the orthosis 205 can also include and/or otherwise be operably coupled to one or more sensors 230, as shown and described herein with reference to FIGS. 7 and 8. The frame 210 of the orthosis 205 can have any suitable shape and/or size that can be, for example, associated with a segment of the leg 20 and includes at least a portion that can be transitioned between a first configuration and a second configuration to couple the frame 210 to the leg 20. In some embodiments, the frame 210 can have a shape and size that are associated with a portion of the lower leg (e.g., between the knee and the foot of the lower leg). As such, an upper portion of the frame 210 can form an ergonomic contour that can, for example, substantially correspond with a shape of an inferior border of a patella 21 of a knee of the leg 20 (see e.g., FIG. 4). Moreover, the frame 210 can define an ergonomic cross-sectional shape taken about a plane that is normal to a longitudinal axis of the frame 210 (e.g., substantially coaxial with an axis defined by the segment of the leg 20) that corresponds to and/or otherwise is associated with a shape of a tibial crest 22 of the lower leg (see e.g., FIG. 4). In some embodiments, the frame 210 can be substantially similar in form and/or function as those described in the '556 patent, the '036 patent, and/or the '597 patent.

Figure 2:
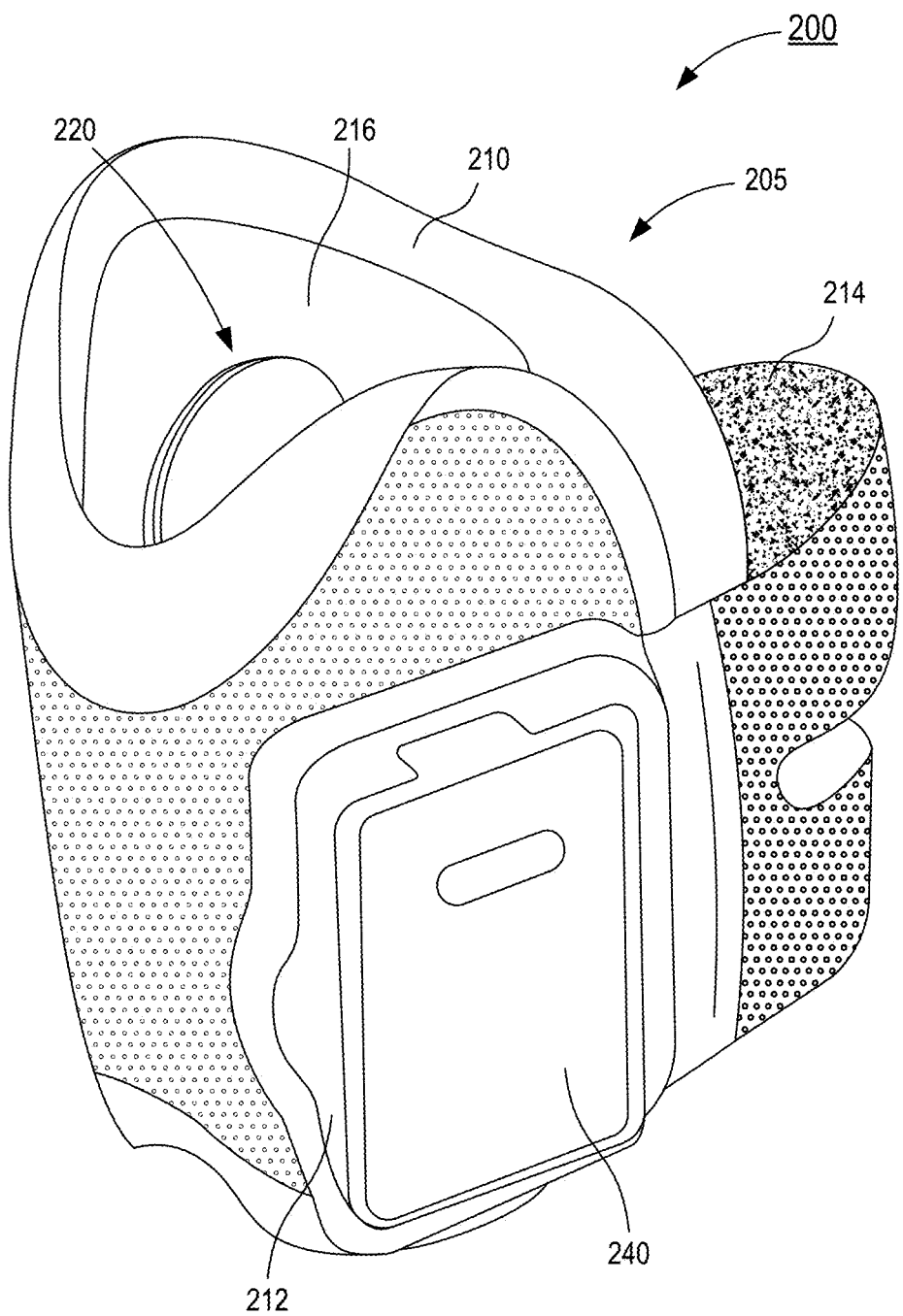
FIG. 2 is a perspective view of a functional electrical stimulation (FES) orthosis for gait modulation according to an embodiment.
Figure 3:
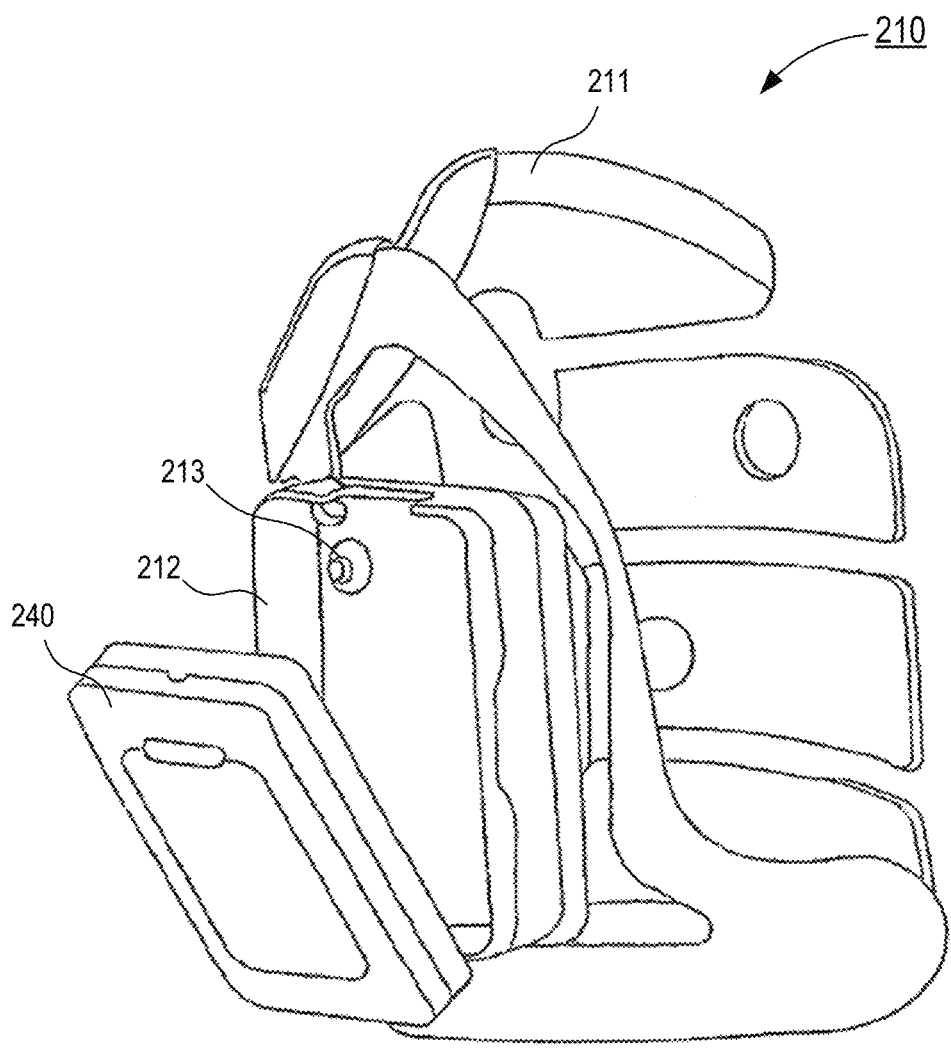
FIG. 3 is a perspective view of a portion of the FES orthosis of FIG. 2 illustrating coupling an electric stimulator to a frame.

As shown in FIGS. 2-5, the frame 210 includes an inner structure 211, a cradle 212, a coupling portion 214, and a cover 216. At least a portion of the inner structure 211 can be formed from a semi-rigid material such as, for example, a relatively thin metal, a thermoplastic, a polymer, and/or the like. In this manner, the inner structure 211 can be sufficiently rigid to provide structural support for the orthosis 205, while being sufficiently flexible to allow the limb about which the inner structure 211 is disposed to increase or decrease during, for example, muscle flexion or muscle relaxation, respectively. As shown in FIG. 3, the inner structure 211 can be substantially C-shaped such as to allow the inner structure 211 to expand and contract in response to the expansion and contraction of the leg 20, respectively. Moreover, the arrangement of the inner structure 211 can be such that when the size of the leg 20 is reduced (e.g., after expansion due to muscle flexion), the rigidity of the inner structure 211 can be sufficient to transition the inner structure 211 to a size and shape associated with the reduced size of the leg 20. Similarly stated, the inner structure 211 be biased such that when an external force expands the inner structure 211 to an expanded size is removed, the inner structure 211 returns to an unexpanded size, smaller than the expanded size. Thus, this arrangement enables the frame 210 to substantially envelop the portion of the leg 20, and serves to effectively disperse a pressure and/or strain that would otherwise be exerted on the portion of the leg 20, thereby retaining the natural profile and geometry of the leg 20 tissue and/or muscles when coupled thereto. In some embodiments, the inner structure 210 can be substantially similar in form and/or function as a central frame described in the '556 patent, the '036 patent, and/or the '597 patent.

Figure 4:
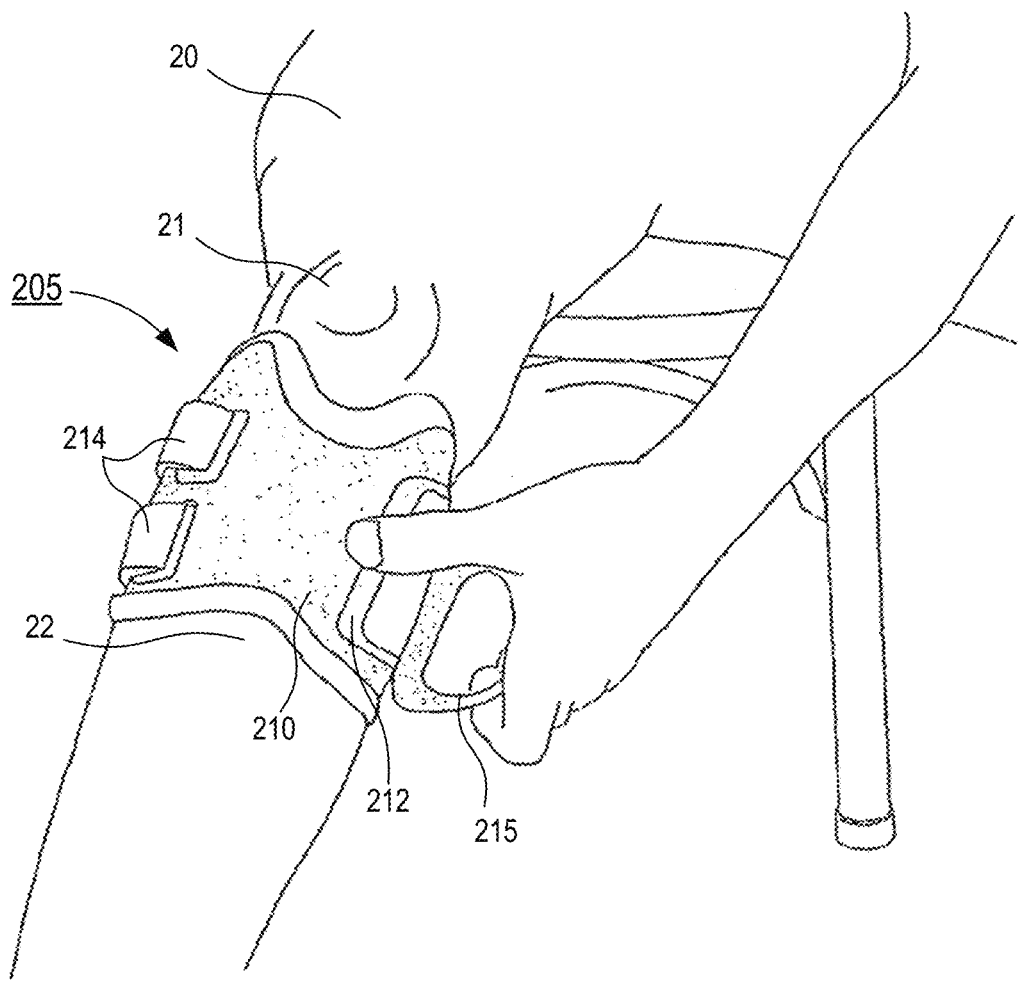
FIG. 4 illustrates a portion of a patient donning the FES orthosis of FIG. 2 on an impaired leg.

The cradle 212 of the frame 210 extends from the inner structure 211 to define a recess within which the electric stimulator 240 can be disposed. Similarly stated, the cradle 212 includes and/or is otherwise formed by a relatively thin set of walls extending from an outer surface of the inner structure 211 that have a size and a shape that are associated with the electric stimulator 240. The cradle 212 can include any suitable surface finish, protrusion, detent, etc. that can act to at least temporarily retain the electric stimulator 240 within the walls forming the cradle 212. For example, in some embodiments, the cradle 212 can form and/or define a set of detents that can matingly receive a set of corresponding protrusions extending from an outer surface of the electric stimulator 240 when therein (or vice versa). In other embodiments, an inner surface of the cradle 212 can have a finish and/or can be formed from a material with a relatively high coefficient of friction. Thus, when the electric stimulator 240 is disposed within the cradle 212 an outer surface of the electric stimulator 240 and an inner surface of the cradle 212 can form and/or define a friction fit that can at least temporarily retain the electric stimulator 240 in the cradle 212. As shown in FIGS. 3 and 4, the cradle 212 includes and/or forms a connector 213 that can be electrically coupled to a corresponding connector (not shown in FIGS. 2-8) of the electric stimulator 240. Moreover, the connector 213 is electrically coupled to a connector 222 of the electrode assembly 220 (described in further detail herein). Therefore, when the electric stimulator 240 is positioned within the cradle 212, the connector 213 can place the electric stimulator 240 in electrical communication with the electrode assembly 220, as described in further detail herein. Although described above as electrically connecting the electric stimulator 240 to the electrode assembly 220, in some embodiments, the connector 213 can be configured to electrically connect any number of electrical devices (e.g., one or more sensors and/or the like) to the electric stimulator 240 and/or the electrode assembly 220.

The coupling portion 214 of the frame 210 can be transitioned between a first (e.g., open) configuration and a second (e.g., closed) configuration to reversibly couple the frame 210 to the leg 20. Said another way, the frame 210 can be positioned about a portion of the leg 20 and the coupling portion 214 can be transitioned to the second configuration to removably couple (i.e., at least temporarily couple) the frame 210 to the leg 20, as shown in FIG. 4. The coupling portion 214 includes substantially parallel, modular straps (e.g., elastic straps, inelastic straps, and/or straps including one or more elastic portions and one or more inelastic portions) connecting between the frame 210 and a handle 215. The arrangement of the coupling portion 214 is such that during donning, the straps wrap circumferentially around the limb segment (e.g., the leg 20), to securely couple the orthosis 205 to the limb segment. In some embodiments, the handle 215 can form and/or provide a structure that can facilitate the engagement of the coupling portion 214. For example, in some embodiments, the handle can facilitate the engagement and/or manipulation of the coupling portion 214 by a patient who may have impairment in one or both hands.

Figure 6:
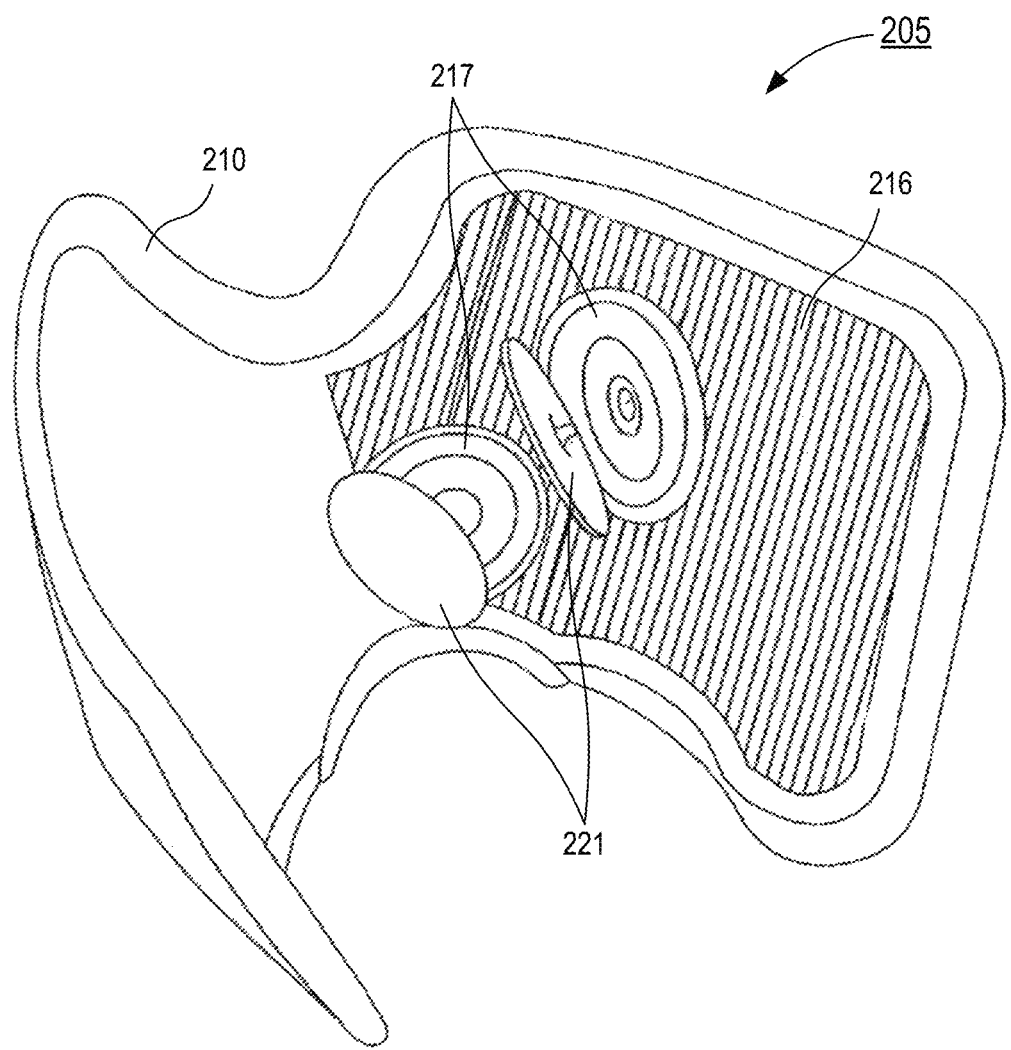
FIG. 6 is a rear perspective view of the FES orthosis of FIG. 2 illustrating the electrode assembly of FIG. 5 coupled to an inner surface of the frame of FIGS. 3-5.

The cover 216 of the frame 210 can be configured to substantially enclose the inner structure 211 and includes an (see e.g., FIGS. 2 and 6). The cover 216 can be formed from any suitable material and/or combination of materials. For example, in some embodiments, the cover 216 can be formed from a relatively flexible and/or soft material that can elastically deform when exposed to an external force. In some embodiments, the cover 216 can be, for example, over-molded about the inner structure 211. In other embodiments, the cover 216 can be removably disposed about the inner structure 211. In this manner, the cover 216 can enhance the ergonomics (e.g., comfort) of the frame 210 by forming a relatively flexible and/or soft layer that is placed in contact with the patient.

Figure 5:
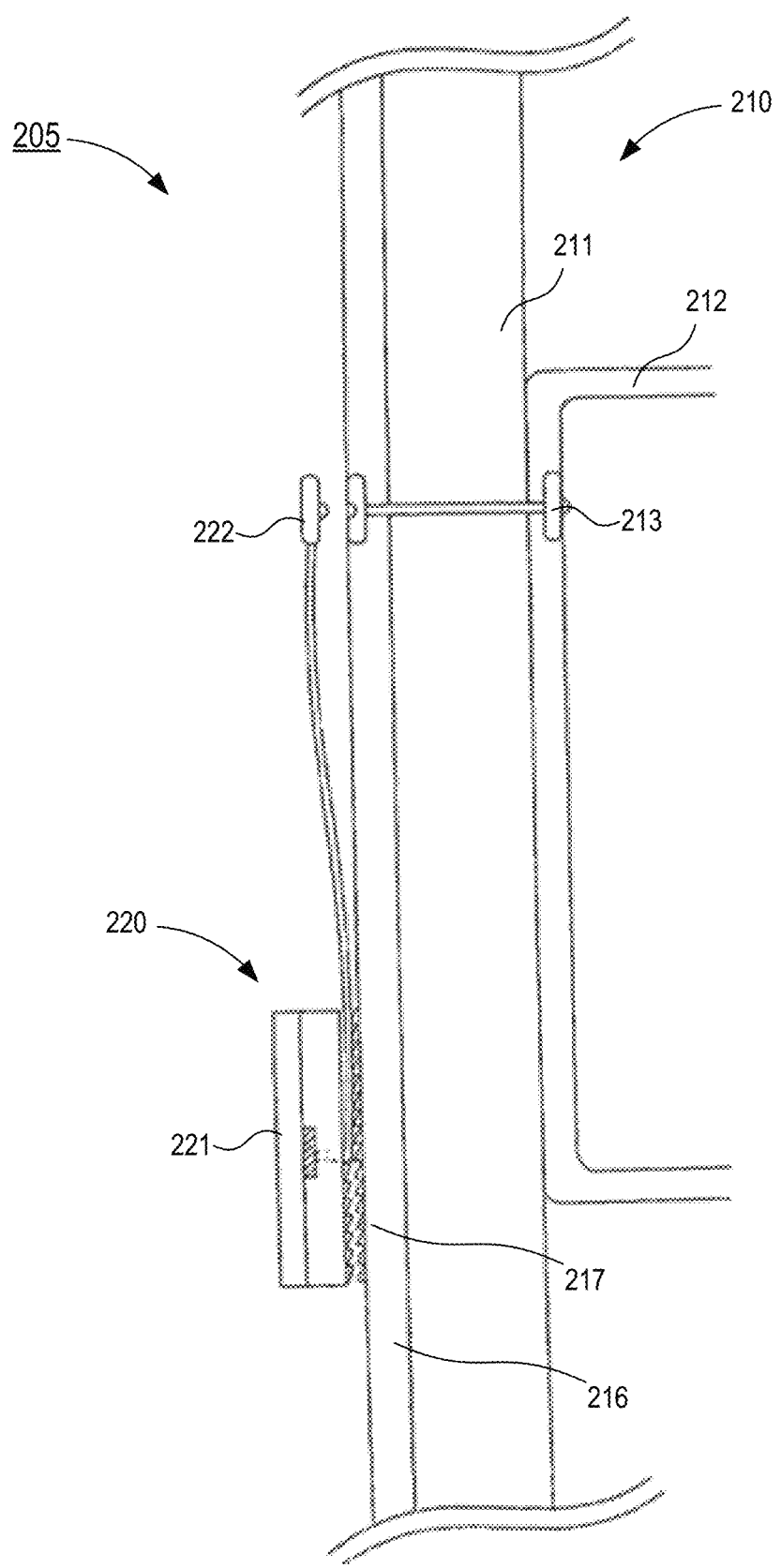
FIG. 5 is a schematic side view of a portion of the FES orthosis of FIG. 2 illustrating an electrical connection between the electric stimulator of FIG. 3 and an electrode assembly.

As shown in FIGS. 5 and 6, the cover 216 includes one or more couplers 217 that can engage a portion of the electrode assembly 220. The couplers 217 can be any suitable shape, size, or configuration. For example, in some embodiments, the couplers 217 can form a button, a snap, a detent, a protrusion, one half of a hook-and-loop coupler (i.e., Velcro®), and/or the like. As such, the couplers 217 can each be matingly placed in contact with a corresponding portion of a different electrode 221 included in the electrode assembly 220 to at least temporarily retain the electrodes 221 in a substantially fixed position relative to the frame 210. In some embodiments, the position of the couplers 217, and hence the electrodes 221 coupled thereto, can be associated with a target portion of the neuromuscular system of the leg 20 such as, for example, the peroneal nerve and/or the tibial nerve. Thus, when the electric stimulator 240 is disposed in the cradle 212 of the frame 210, the connector 213 of the inner structure 211 and the connector 222 of the electrode assembly 220 (described above) electrically couple the electric stimulator 240 to the electrodes 221 such that a relatively high current can flow from the electric stimulator 240 and through the electrodes 221 to provide functional electrical stimulation to the portion of the neuromuscular system of the leg 20, as described in further detail herein.

Although the electrodes 221 are particularly shown and described with reference to FIGS. 5 and 6, in other embodiments, the electrodes 221 can be any suitable configuration. For example, in some embodiments, the orthosis 205 can include one, two, three, four, five, six, or more electrodes disposed at different positions along the inner surface of the cover 216. Moreover, while the inner surface of the cover 216 is shown as including discrete couplers 217, in other embodiments, any number of electrodes 221 can be coupled directly to the inner surface and retained in a substantially fixed position relative to the frame 210. In some embodiments, the electrodes 221 and/or the electrode assembly 220 can be substantially similar in form and function as those described in the '556 patent, the '036 patent, and/or the '597 patent.

The sensor 230 (see e.g., FIG. 7) of the orthosis 205 can be any suitable sensor device or can include a combination of sensor devices. For example, in some embodiments, the sensor 230 can include a tilt sensor, an accelerometer, a gyroscope, a pressure sensor, a speedometer, and/or the like. In this manner, when the system 200 is used for gait modulation of a patient with the impaired leg 20, the sensor 230 can be configured to sense and/or otherwise detect a characteristic associated with, for example, a gait event such as position of the sensor 230 relative to the orthosis 205, position of the leg 20 relative to a reference plane or the like, angular position of the leg 20 relative to a reference plane or the like, velocity, rate of change in velocity (i.e., acceleration), tilt of the patient's foot, pressure (e.g., when the foot and/or shoe contacts a surface upon which the patient is walking), etc.

As described above, in some embodiments, the sensor 230 can be included in and/or integrated with the frame 210, the electrode assembly 220, and/or the electric stimulator 240. In other embodiments, the sensor 230 can be physically distinct from the orthosis 205 and in electrical communication with the electric stimulator 240 via a wireless communication channel. For example, in some embodiments, the electric stimulator 240 can be coupled to the frame 210, which in turn, is coupled to a first segment of the leg 20 (e.g., adjacent to the knee of the patient as shown in FIG. 4) and the sensor 230 can be coupled to and/or otherwise can be associated with a second segment of the leg 20 (e.g., adjacent to the foot and/or ankle of the patient's impaired leg). By way of example, the sensor 230 can be at least temporarily coupled the patient's shoe worn on the foot of the impaired leg 20 (see e.g., FIG. 8). In some embodiments, the sensor 230 can be coupled and/or otherwise can be associated with a segment of the contralateral leg (e.g., adjacent to the foot and/or ankle of the patient's leg not donning the electric stimulator 240). In some embodiments, the system 200 can include multiple distinct sensors 230. For example, in some embodiments, the system 200 can include a first sensor that is integrated with the electric stimulator 240 and a second sensor that is physically distinct from, yet in electrical communication with, the electric stimulator 240 (e.g., disposed within and/or coupled to a shoe of the patient). In such embodiments, the electrical stimulator 240 can be configured to receive signals from and/or send signals to the first sensor via a first communication channel, associated with a wired signal transmission (e.g., signals transmitted along a wire or signal trace), and a second communication channel, associated with a wireless signal transmission (e.g., WiFi®, Bluetooth®, etc.), as described in further detail herein.

In some embodiments, the sensor 230 can be substantially similar in form and/or function as those described in U.S. Pat. No. 7,632,239 entitled, "Sensor Device for Gait Enhancement," filed Oct. 23, 2006, U.S. Pat. No. 8,382,688 entitled, "Sensor Device for Gait Enhancement," filed Dec. 4, 2009, and U.S. Patent Application Publication No. 2009/0069865 entitled, "Functional Electrical Stimulation Systems," filed May 1, 2007, the disclosures of which are incorporated herein by reference in their entireties.

Figure 7:
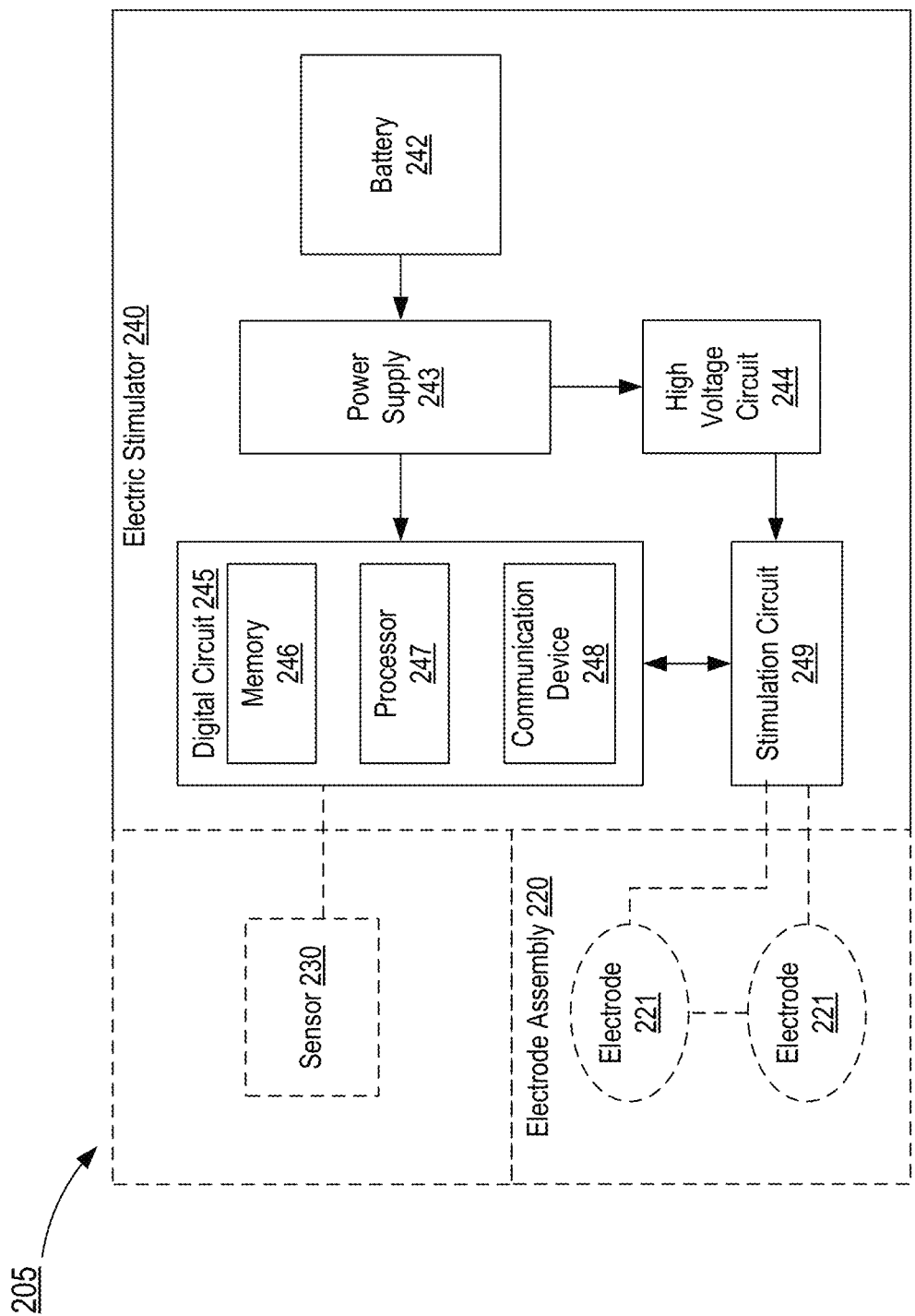
FIG. 7 is a schematic block diagram illustrating an electrical system of the FES orthosis of FIG. 2.

The electric stimulator 240 can be any suitable electronic device configured to generate a flow of a relatively high current. As described above, the electric stimulator 240 can be positioned within the cradle 212 of the frame 210 to at least temporarily couple the electric stimulator 240 thereto. As shown in FIG. 7, the electric stimulator 240 includes a battery 242 and a power supply 243 that are in electrical communication with a high voltage circuit 244, a digital circuit 245, and a stimulation circuit 249. The battery 242 can be any suitable battery and/or other source of electrical power. For example, in some embodiments, the battery 242 can be a relatively low profile rechargeable battery (e.g., a coin battery or the like). Similarly, the power supply 243 can be any suitable power supply, converter, conditioner, inverter, capacitor, and/or the like. The power supply 243 can be electrically coupled to the battery 242 via any suitable circuit and/or interface. In this manner, the power supply 243 can receive a flow of electrical current from the battery 242 and convert, amplify, condition, and/or otherwise change one or more attributes associated with the electrical current received from the battery 242. For example, in some embodiments, the power supply 243 can be configured to increase a voltage associated with at least a portion of the electrical current received from the battery 242.

In some embodiments, the power supply 243 can receive electrical current from the battery 242 and can, for example, increase and/or convert a voltage of a first portion of the electrical current by a first amount (e.g., to a first voltage), and increase and/or convert a voltage of a second portion of the electrical current by a second amount (e.g., to a second voltage), less than the first amount. In such embodiments, the power supply 243 can include a first electrical circuit (not shown in FIG. 7) that is associated with the first voltage (i.e., the higher voltage) and that is electrically coupled to the high voltage circuit 244. Similarly, the power supply 243 can include a second electrical circuit (not shown in FIG. 7) that is associated with the second voltage (i.e., the lower voltage) and that is electrically coupled to the digital circuit 246. Thus, the power supply 243 can receive a flow of current from the battery 242 and can convert the flow of current into a first portion having a relatively high voltage suitable for the high voltage circuit and a second portion having a relatively low voltage suitable for the digital circuit.

The high voltage circuit 244 can include any suitable electrical component. For example, although not shown in FIG. 7, the high voltage circuit 244 can include a capacitor, resistor, logic gate, wire, electrical trace, and/or the like. The high voltage circuit 244 is in electrical communication with the stimulation circuit 245 and is configured to provide a flow of electrical current having the relatively high voltage (described above) thereto.

The digital circuit 245 can be any suitable electrical circuit including any suitable electrical component. For example, as shown in FIG. 7, the digital circuit 245 includes at least a memory 246, a processor 247, and a communication device 248 that are each electrically coupled via, for example, a set of wires, signal traces, and/or the like (not shown in FIG. 7). Although not shown in FIG. 7, the digital circuit 245 can also include one or more sensors 230 that can be in electrical communication with the memory 246, the processor 247, and/or the communication device 248 via the set of wires, signal traces, and/or the like. Moreover, the components of the digital circuit 245 can be in electrically coupled to the power supply 243 via one or more wires, signal traces, and/or the like.

The memory 246 can be, for example, a random access memory (RAM), a memory buffer, a hard drive, a read-only memory (ROM), an erasable programmable read-only memory (EPROM), and/or the like. In some embodiments, the memory 246 can be configured to store, for example, one or more modules that can include instructions to cause the processor 247 to perform one or more processes, functions, and/or the like. For example, in some embodiments, the memory 246 can store instructions and/or code representing one or more parameters associated with providing FES to a patient, as described in further detail herein.

The processor 247 of the digital circuit 245 can be any suitable processing device configured to run and/or execute a set of instructions or code such as, for example, a general purpose processor (GPU), a central processing unit (CPU), an accelerated processing unit (APU), an application specific integrated circuit (ASIC), a front end processor, a field programmable gate array (FPGA), and/or the like. As such, the memory 246 can store instructions to cause the processor 247 to execute modules, processes, and/or functions associated with providing FES to the patient. In this manner, based on the instructions stored by the memory 246, the processor 247 can change, modify, update, and/or otherwise control one or more parameters associated with FES. For example, in some instances, the memory 246 can include instructions to cause the processor 247 to perform one or more functions, processes, and/or modules based on receiving a signal from the sensor 230 (e.g., in communication with the digital circuit 245, as described in further detail herein). In some such instances, the functions, processes, and/or modules can be operable in providing and/or terminating a flow of relatively high current to the electrode assembly 220, as described in further detail herein.

The communication device 248 of the digital circuit 245 can be any suitable device that can communicate with one or more electrical components and/or with one or more networks. For example, the communication device 248 can include one or more wired and/or wireless interfaces, such as, for example, Ethernet interfaces, optical carrier (OC) interfaces, and/or asynchronous transfer mode (ATM) interfaces. In some embodiments, the communication device 248 can be, for example, a network interface card and/or the like that can include at least an Ethernet port and/or a wireless radio (e.g., a WiFi® radio, a Bluetooth® radio, cellular network radio (e.g., global system for mobile communications (GSM), personal communications service (PCS), digital advanced mobile phone service (D-AMPS), etc.). In this manner, the communication device 248 can be configured to place the orthosis 205 in electrical communication (e.g., via a wired or wireless connection) with any suitable external device such as, for example, a control device, a sensor, a second orthosis (similar to or different from the orthosis 205), and/or the like via one or more networks. Such a network can be, for example, a local area network (LAN), a wide area network (WAN), a metropolitan area network (MAN), a worldwide interoperability for microwave access network (WiMAX), a telephone network, an intranet, the Internet, an optical fiber (or fiber optic)-based network, a virtual network, a cellular network (e.g., GSM, PCS, D-AMPS, etc.), and/or any other suitable network. By way of example, in some embodiments, the communication device 248 can be configured to receive signals from and/or send signals to the sensor 230 coupled to the shoe worn on the foot of the impaired leg 20 via Bluetooth® (see e.g., FIG. 8).

As shown in FIG. 7, the stimulation circuit 249 is in electrical communication with the high voltage circuit 244 and the digital circuit 245. The stimulation circuit 249 can include any suitable electrical component. For example, although not shown in FIG. 7, the stimulation circuit 249 can include a capacitor, a resistor, a logic gate, a wire, an electrical trace, and/or the like. Moreover, the stimulation circuit 249 is electrically coupled to the electrode assembly 220. In this manner, the stimulator circuit 249 can receive a flow of relatively high current and can transmit the relatively high current to the electrodes 221 to, for example, provide FES to the leg 20. In some embodiments, the digital circuit 245 can be configured to send a signal to the stimulation circuit 249 that can, for example, control the output of the stimulation circuit 249. For example, the stimulation circuit 249 can include a component, processor, logic gate, and/or the like that can operable in switch the stimulation circuit 249 between a first configuration and a second configuration based on receiving or not receiving a signal from the digital circuit 245. By way of example, the first configuration can be associated with an open circuit or the like in which upon receiving the flow of current (i.e., the relatively high current) from the high voltage circuit 244, the stimulation circuit 249 does not transfer, transmit, and/or otherwise provide a flow of relatively high current to the electrode assembly 220. Conversely, the stimulation circuit 249 can receive a signal (e.g., a relatively low voltage electrical current signal) from the digital circuit 245 that can be operable in switching the stimulation circuit to its second configuration, which can be associated with a closed circuit or the like. Thus, when in the second configuration and upon receiving the flow of current from the high voltage circuit 244, the closed stimulation circuit 249 can transmit, transfer, and/or otherwise provide a flow of relatively high current to the electrode assembly 220. As such, the electrode assembly 220 can provide FES (via the electrodes 221) to a portion of the neuromuscular system of the leg 20.

As described above, in some instances, the system 200 can be used for gait modulation of the patient having the impaired leg 20. More specifically, the system 200 can be used to enhance the leg 20 function of the patient experiencing drop foot. In such instances, the patient can manipulate the orthosis 205 in such a manner as to couple the orthosis 205 to the impaired leg 20. For example, the patient can position the orthosis 205 adjacent to the patella 21 of the impaired leg 20 and can transition the coupling portion 214 of the frame 210 from its first configuration to its second configuration to removably couple the orthosis 205 to the leg 20, as described above with reference to FIG. 4. The placement of the orthosis 205 can be such that the electrodes 221 included in the electrode assembly 220 are disposed in a location relative to the leg 20 that is associated with and/or corresponds to the peroneal nerve and/or the tibial nerve. Thus, the electrodes 221 can transmit functional electrical stimulation to the peroneal nerve, which can result in dorsiflexion of the foot, and/or the tibial nerve, which can result in plantarflexion of the foot, thereby enhancing the function of the impaired leg 20 to mitigate the effects of lower leg weakness, lower leg paralysis, and/or drop foot With the frame 210 retained in the desired position relative to the impaired leg 20 via the inner structure 211 and the coupling portion 214, the patient can begin walking. During walking, the sensor 230 can be configured to sense and/or detect a set of characteristics (such as those described above) associated with a gait event and can send a signal associated with the characteristic to the electric stimulator 240. For example, in some embodiments, the sensor 230 can be coupled to and/or disposed in a shoe worn on the foot of the impaired leg 20 and can be configured to sense and/or detect a gait event associated with a "heel-off" event based at least in part on a change in pressure. The sensor 230 can then send the signal to the electric stimulator 240 via, for example, a protected wireless communication channel.

In other embodiments, the sensor 230 can be collocated with at least a portion of the electric stimulator 240 and/or the frame 210. As such, the sensor 230 can be configured to sense and/or detect the "heel-off" event based at least in part on an acceleration, tilt, relative position, and/or movement of the sensor 230. In this manner, the sensor 230 can send a signal via a communication channel associated with a wired signal transmission to the electric stimulator 240. In still other embodiments, the electric stimulator 240 can receive a signal from multiple sensors 230 that can be configured to sense and/or detect a characteristic associated with a gait event at different segments along the leg of the patient. For example, the electric stimulator 240 can receive a signal from a collocated sensor 230 via a first communication channel associated with a wired signal transmission and can receive a signal from a physically distinct sensor 230 via a second communication channel associated with a wireless signal transmission such as, for example, Bluetooth®.

In this manner, the communication device 248 of the electric stimulator 240 can receive the signal from the sensor 230 and can forward the signal and/or otherwise send a signal representing the received signal to the processor 247. Upon receipt, the processor 248 can determine, reference, and/or calculate one or more system parameters based at least in part on information stored in the memory 246 and the signal sent from the sensor 230. In some instances, the processor 247 can perform one or more processes, functions, modules and/or the like that can, for example, cause the power supply 243 to generate and transmit a relatively high current along the high voltage circuit 244 to the stimulation circuit 249. In addition and substantially in a parallel process, the processor 247 can send a relatively low voltage electrical current signal to the stimulation circuit 249 that can, for example, place the stimulation circuit 249 in a closed state or the like. Thus, the relatively high current is transmitted to the electrodes 221 of the electrode assembly 220, which in turn provides FES to the peroneal nerve, thereby resulting in dorsiflexion of the foot substantially at the time of the heel-off event (e.g., a very short time after the sensor 230 detects the heel-off event as described above). As a result, the foot of the patient flexes toward the leg, enhancing a portion of the patient's gait.

In some instances, the sensor 230 can sense and/or detect a characteristic associated with a second gait event such as, for example, a "heel-on" event (i.e., the point during gait at which the heel is placed in contact with the surface of upon which the patient is walking). As described above, the sensor 230 can send a signal associated with the characteristic to the electric stimulator 240 and, upon receipt, the processor 247 can send a signal to the power supply 243 to terminate the flow of the relatively high current to the high voltage circuit 244. In addition and in a substantially parallel process, the processor 247 can send a relatively low voltage electrical current signal to the stimulation circuit 249 that can, for example, place the stimulation circuit 249 in an open circuit state or the like. Thus, current is no longer transferred to the electrodes 221 in electrical contact with the peroneal nerve, thereby allowing the associated muscles to relax, which in turn results in the foot moving in a direction away from the leg. In this manner, the FES provided to the peroneal nerve can facilitate the gait of the patient.

In other instances, the processor 247 need not send a signal to the power supply 243 to terminate the flow of relatively high current to the high voltage circuit 244. For example, in such instances, the stimulation circuit 249 can define multiple electrical circuits between the stimulation circuit 249 and different portions of the electrode assembly 240. In this manner, the processor 247 can send a signal to the stimulation circuit 249 that can be operable in opening the electrical circuit associated with the peroneal nerve, thereby terminating the FES provided thereto, and can be operable in closing a different electrical circuit associated with, for example, the tibial nerve. Thus, the relatively high current can flow along the now closed electric circuit that is electrically coupled to one or more electrodes 221 in electrical communication with the tibial nerve. As such, the electrodes 221 can provide FES to the tibial nerve resulting in plantarflexion of the foot substantially at the time of the heel-on event (as described above). More specifically, the termination of the FES to the peroneal nerve relaxes the portion of the neuromuscular system resulting in a relaxation of the dorsiflexion, while substantially concurrently, the FES provided to the tibial nerve results in plantarflexion of the foot. As a result, the foot flexes away from the leg, enhancing the patient's gait.

In some embodiments, the memory 246 of the digital circuit 245 can store information at least partially defining a set parameters associated with the FES. For example, in some embodiments, the memory 246 can store information associated with a voltage and/or current level associated with the FES, a sensitivity associated with the sensor 230, a repository of actions to perform based on information received from the sensor 230, a skin sensitivity of the patient, and/or any other suitable information and/or logic. Thus, the electric stimulator 240 can be configured to provide FES to the impaired leg 20 with a set of characteristics that can be uniquely associated with the patient. In some instances, the patient and/or a health care professional can manipulate the electric stimulator 240 to change one or more parameters and/or characteristics associated with the FES provided to the impaired leg 20. For example, although not shown in FIGS. 2-8, in some embodiments, the electric stimulator 240 can include an output device such as, for example, a display. In some instances, the display can, for example, provide a user interface for the patient and/or the health care professional to monitor, modify, and/or otherwise control the electric stimulator 240.

Although the electric stimulator 240 is described above as providing FES to, for example, a first portion of the neuromuscular system of the patient, and upon receiving a signal from the sensor 230, terminating the FES to the first portion of the neuromuscular system and providing FES to, for example, a second portion of the neuromuscular system, in other embodiments, the electric stimulator 240 can be configured to provide FES to the first portion and the second portion of the neuromuscular system in substantially concurrent and/or complementary processes. Moreover, the processor 247 can be configured to perform and/or execute one or more processes, functions, and/or modules associated with selectively modulating a flow of electrical current to one or more portions of the neuromuscular system. For example, in some embodiments, the electric stimulator 240 can be configured to provide FES to a portion of the peroneal nerve, which can result in dorsiflexion of the foot on an impaired leg. Based at least in part on a signal received from the sensor 230, the processor 247 can perform one or more processes and/or functions that can, for example, reduce a voltage of the FES that is provided to the portion of the peroneal nerve, thereby reducing dorsiflexion of the foot. In a substantially parallel and/or concurrent process, the processor 247 can execute one or more functions that can close a circuit (e.g., within the stimulation circuit 249) or the like to provide FES to a second portion of the neuromuscular system (e.g., a second portion of the peroneal nerve and/or a portion of the tibial nerve) that can result in plantarflexion of the foot. In some instances, a voltage associated with the FES provided to cause plantarflexion can be increased in a substantially concurrent and/or inversely proportional process as the decrease in the voltage of the FES provided to cause dorsiflexion. In this manner, the processor 247 of the electric stimulator 240 can be configured to direct, divert, steer, and/or otherwise control a flow of current through, for example, the stimulation circuit 249 to selectively provide at least a portion of the flow of current to the electrode assembly 220.

In some embodiments, the electrode assembly 220 can include one or more electrodes in electrical communication with a portion of the neuromuscular system that is associated with eversion or inversion of the foot. In such embodiments, a sensor (e.g., the sensor 230) can sense and/or determine a characteristic associated with eversion or inversion of the foot of an impaired leg and can send a signal associated with the characteristic to the electric stimulator 240. In this manner, the processor 247 can be configured to perform or execute one or more functions, processes, modules, and/or the like that is associated with directing, diverting, and/or otherwise controlling a flow of current through the stimulation circuit 249 such that a desired amount of FES is provided to the portion of the neuromuscular system controlling eversion and inversion (e.g., superficial portions of the peroneal nerve and/or the like).

In some embodiments, the electrode assembly 220 can include a set of electrodes, with each electrode being in electrical communication with a different portion of the neuromuscular system. Moreover, the electrode assembly 220 can be electrically coupled to the electric stimulator 240 such that each electrode is in electrical connection with a different electric communication channel of the electric stimulator 240. In this manner, the set of electrodes can define and/or bound an area of stimulation to be applied to, for example, an impaired limb. As described above, the processor 247 can be configured to execute a set of instructions (e.g., stored in the memory 246) associated with increasing or decreasing a voltage provided to each electrode in a substantially concurrent process based at least in part on a signal received from the sensor 230 (or multiple sensors). Thus, the electric stimulator 240 can direct, steer, divert, and/or otherwise control (i.e., increase or decrease) a voltage provided to the set of electrodes to continuously control (e.g., during gait) an amount of dorsiflexion, plantarflexion, eversion, inversion, and/or the like to, for example, increase a stability of the impaired limb and/or the patient during gait.

Figure 8:
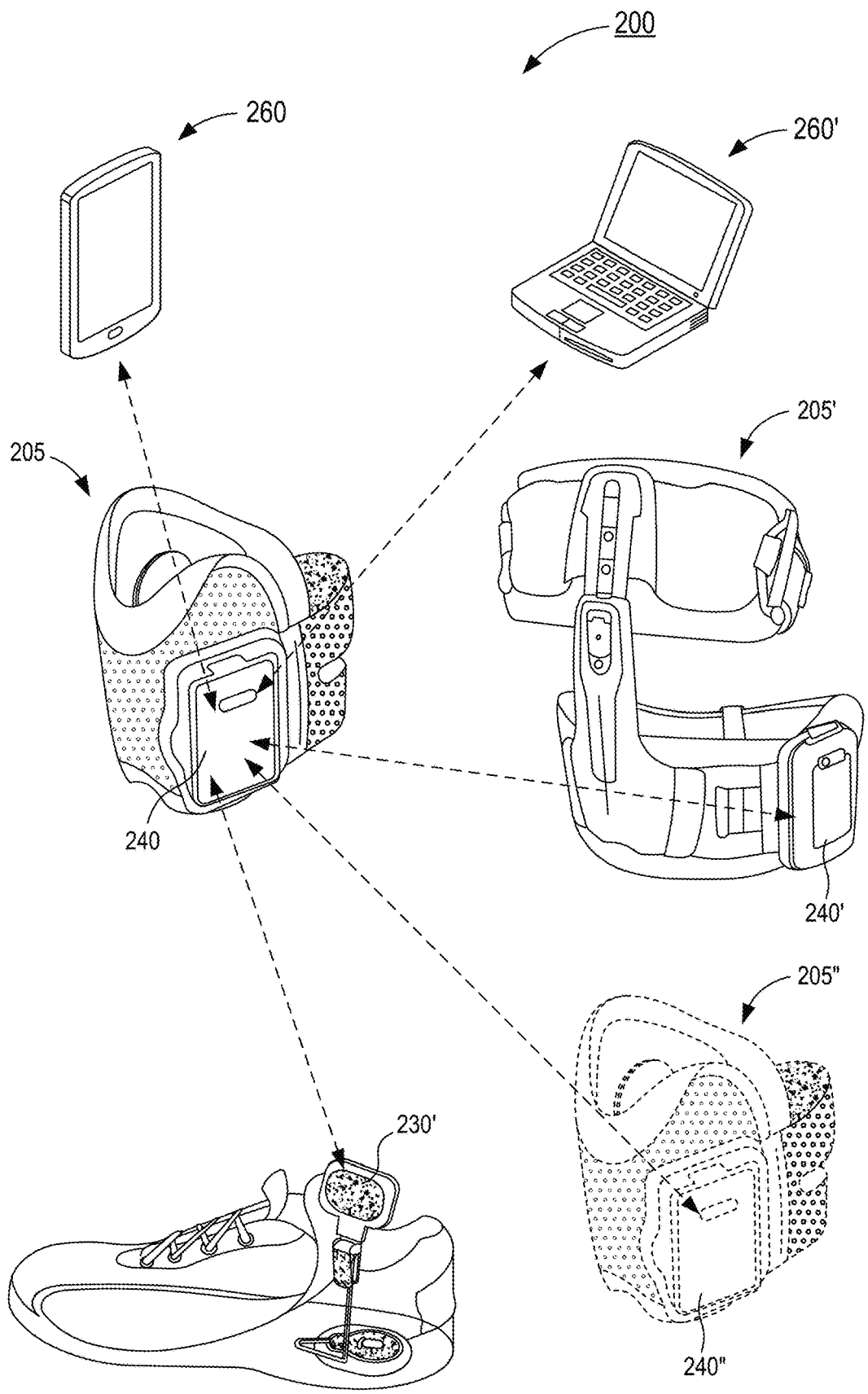
FIG. 8 illustrates the FES orthosis of FIG. 2 included in a system for gait modulation.

As shown in FIG. 8, in some embodiments, the electric stimulator 240 can be in communication with one or more control devices 260 and 260'. The control device 260 can be any suitable electronic device that can provide an interface for a user (e.g., the patient and/or a health care professional) to manipulate one or more characteristics and/or parameters associated with the FES. For example, in some embodiments, the control device 260 can be, for example, a smart phone or the like that can be manipulated to run and/or execute a set of instructions associated with controlling the electric stimulator 240. Similarly, the control device 260' can be a personal computer (PC), a laptop, a tablet PC, a server device, a workstation, and/or the like that can be manipulated to run and/or execute a set of instructions associated with controlling the electric stimulator 240. In some instances, the control device 260 can be in communication with the electric stimulator 240 via the communication device 248. Although shown in FIG. 8 as being in communication with one or more control devices, in other embodiments, the electric stimulator 240 can include any suitable hardware and/or software that can, for example, enable to the electric stimulator to function as a control device. For example, in some embodiments, the electric stimulator 240 can include a user interface and/or the like that can be manipulated by a user to control at least a portion of the electric stimulator 240.

In some instances, the electric stimulator 240 can be configured to communication with any number of electronic devices. For example, in some embodiments, the electric stimulator 240 can be in electrical communication with the control devices 260 and 260', a physically distinct sensor 230, and an electric stimulator 240' of a second orthosis 205'. In such embodiments, the electric stimulator 240 and/or the communication device 248 can be configured to communicate with the electronic devices via, for example, unique communication channels. Thus, the control devices 260 and 260', the physically distinct sensor 230, and the orthosis 205 and 205' can collectively provide FES to a patient that can, for example, enhance the patient's gait or the like. More specifically, in some embodiments, the orthosis 205' can be configured to be disposed, for example, about the thigh of the patient donning the orthosis 205 (i.e., the thigh of the impaired leg). The electrodes (not shown) of the orthosis 205' can be, for example, in electrical communication with one or more portions of the neuromuscular system associated with, for example, the hamstring and/or the quadriceps. In some embodiments, the orthosis 205' can be substantially similar to or the same as the devices described in U.S. patent application Ser. No. 13/022,149 entitled, "Adjustable Orthosis for Electrical Stimulation of a Limb," filed Feb. 7, 2011, the disclosure of which is incorporated herein by reference in its entirety. Thus, the electric stimulator 240 can be configured to communicate with the electric stimulator 240' to provide FES to substantially the entirety of an impaired limb of the patient. Moreover, in some embodiments, the electronic stimulator 240' can be substantially similar to or the same as the electric stimulator 240 and as such, can be in direct electric communication with the sensor 230' (e.g., via a wired or wireless connection). In other words, the sensor 230' can be configured to send a signal associated with a gait event to the electric stimulator 240 of the orthosis 205 and the electric stimulator 240' of the orthosis 205.

In some embodiments, the electric stimulator 240 can be in electrical communication with, for example, an electric stimulator 240" of an orthosis 205" disposed about a portion of a contralateral leg, as shown in FIG. 8. For example, in some instances, a patient can have a physical impairment of both legs (either equally impaired or one leg having a greater level of impairment). In such instances, the patient can don the orthosis 205 on a first leg (as described above) and can don the orthosis 205" on a second leg (i.e., the contralateral leg). Thus, the electric stimulator 240 of the orthosis 205 and the electric stimulator 240" of the orthosis 205" can be configured to communicate with each other, with the sensor 230', the control devices 260 and/or 260', and/or the electric stimulator 240' orthosis 205'. Although not shown in FIG. 8, in some embodiments, the electric stimulator 240 can be in electrical communication with an FES orthosis in electrical communication with any suitable portion of the neuromuscular system of the patient. For example, in some embodiments, the electric stimulator 240 of the orthosis 205 can be in electrical communication with an electric stimulator of an orthosis disposed about a portion of an impaired arm and/or the like.

Figure 9:
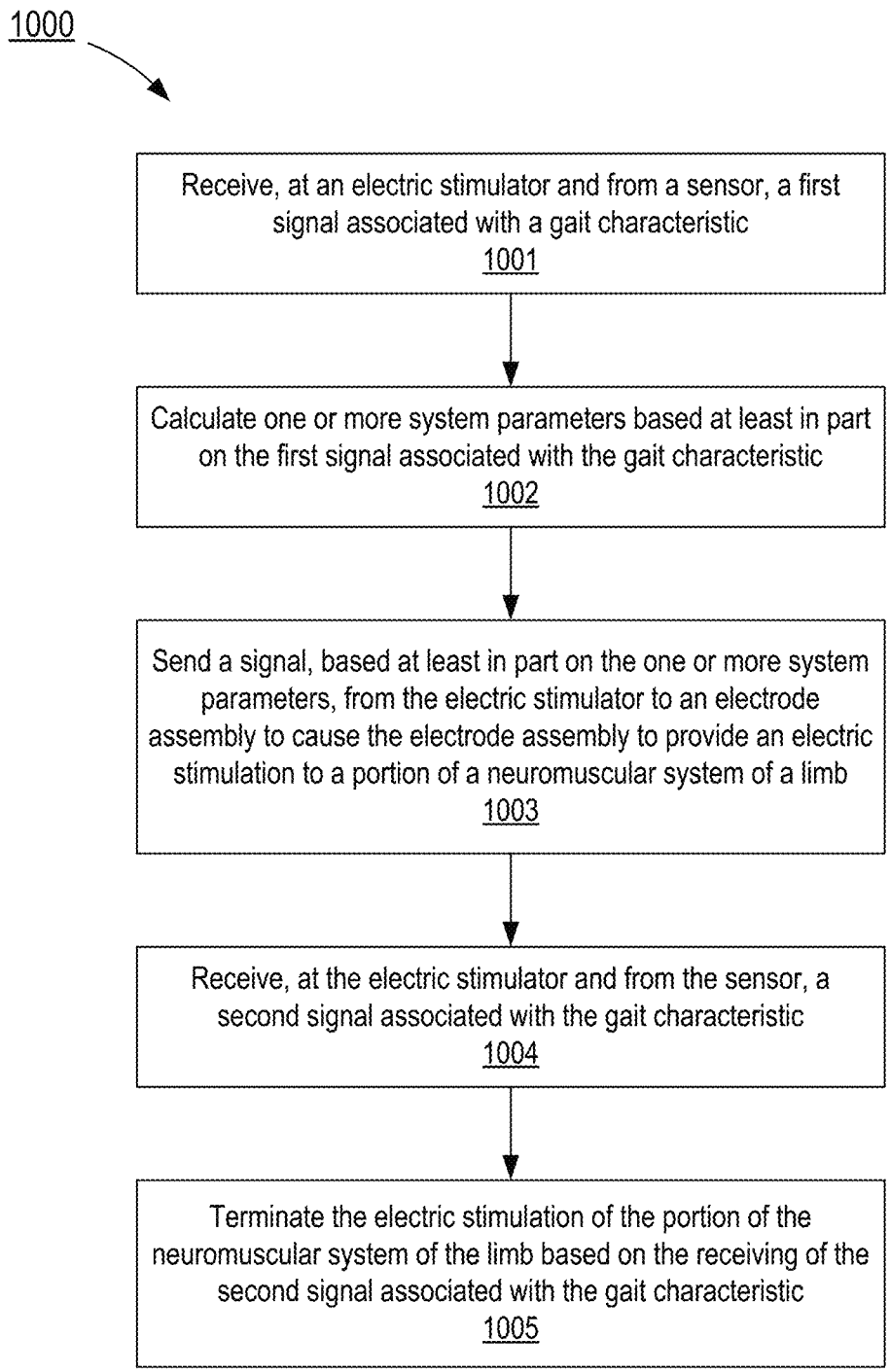
FIG. 9 is a flowchart illustrating a method of using an FES orthosis for gait modulation according to an embodiment.

FIG. 9 is a flowchart illustrating a method 1000 of using an FES orthosis for gait modulation according to an embodiment. The FES orthosis can be any suitable neuroprosthetic and/or the like such as the orthosis 100 and/or 200 described herein. As such, the orthosis can include a frame, an electrode assembly, a sensor, and an electric stimulator, and can be coupled to and/or disposed about an impaired leg of a patient to provide FES thereto. The method 1000 includes receiving, at the electric stimulator and from the sensor, a first signal associated with a gait characteristic, at 1001. For example, in some embodiments, the electric stimulator can be substantially similar in form and function as the electric stimulator 240 described above with reference to FIG. 7. Similarly, the sensor can be substantially similar in form and function as the sensor 230 described above with reference to FIG. 7. In this manner, the sensor can include one or more sensing devices such as, for example, a tilt sensor, pressure sensor, accelerometer, gyroscope, etc. that can sense and/or detect the gait characteristic. In some embodiments, the gait characteristic can be associated with, for example, a "heel-off" event or the like of the impaired leg (e.g., a decrease in pressure as a result of the heel being lifted away from a surface upon which the patient is walking and/or any other suitable characteristic). As such, the sensor can sense and/or detect the gait characteristic and can send the first signal to the electric stimulator. As described above, in some embodiments, the sensor can be integrated with the electric stimulator and as such, the first signal can be sent via a communication channel associated with a wired signal transmission (e.g., along a wire and/or a signal trace). In other embodiments, the sensor can be physically distinct from the electric stimulator, and as such, the first signal can be sent via a communication channel associated with a wireless signal transmission (e.g., WiFi®, Bluetooth®, etc.).

Upon receipt, one or more system parameters are calculated based at least in part on the first signal associated with the gait characteristic, at 1002. For example, in some embodiments, the electric stimulator can include at least a memory and a processor. The memory can store instructions to cause the processor to perform and/or execute one or more functions, processes, modules, and/or the like associated with calculating the one or more system parameters. As such, the processor can receive the first signal from the sensor and can calculate and/or otherwise determine the one or more system parameters associated with that gait characteristic. By way of example, in some embodiments, the memory can include and/or can store a repository that includes a list of gait characteristics and a list of processes and/or functions to be executed by the processor that are associated therewith. In such embodiments, the processor can, for example, query the repository to determine the one or more system parameters associated with the first signal received from the sensor. In other embodiments, the electric stimulator can be in communication with a control device or the like (e.g., via a wired or wireless connection) that can include and/or store the repository. For example, in some embodiments, the control device can be substantially similar to the control device 260 described above with reference to FIG. 8.

Based at least in part on the one or more system parameters, a signal is sent from the electric stimulator to the electrode assembly to cause the electrode assembly to provide an electric stimulation to a portion of the neuromuscular system of the limb, at 1003. For example, in some embodiments, the FES orthosis can be disposed about and/or can at least partially envelop a portion of the impaired leg to substantially align and/or otherwise place one or more electrodes in electrical communication with, for example, the peroneal nerve of the impaired leg. Thus, electric stimulation is provided to a set of muscles associated with the portion of the neuromuscular system of the impaired leg, resulting in dorsiflexion of the foot of the impaired leg (i.e., a pivoting of the foot substantially about the ankle towards the leg).

The method 1000 includes receiving, at the electric stimulator and from the sensor, a second signal associated with the gait characteristic, at 1004. For example, in some embodiments, the gait characteristic can be associated with a "heel-on" event or the like of the impaired leg (e.g., an increase in pressure as a result of the heel being placed in contact with the surface and/or any other suitable characteristic). As such, the sensor can sense and/or detect the gait characteristic and can send the second signal to the electric stimulator.

Based on receiving the second signal associated with the gait characteristic, the electric stimulation of the portion of the neuromuscular system of the limb is terminated, at 1005. For example, in some embodiments, the electric stimulator can be configured to open an electrical circuit between a power supply (e.g., that generates the electric current for stimulation) and the electrode assembly. In other embodiments, the electric stimulator can transition the power supply or the like from an "on" state, in which electrical current is transmitted to the electrode assembly, to an "off" state or the like (e.g., sleep, hibernate, standby, etc.), in which electrical current is not transmitted to the electrode assembly. In still other embodiments, the electric stimulator can modulate an amount of stimulation (e.g., a voltage of the current provided to the electrode assembly) from a first amount resulting in, for example, the dorsiflexion of the limb to a second amount resulting in a substantially relaxing of the portion of the neuromuscular system. Said another way, the electric stimulator can modulate stimulation such that an intensity of the stimulation provided to the portion of the neuromuscular system of the limb is reduced (i.e., the electric stimulator does not substantially terminate the stimulation but reduces the amount of stimulation to a minimal setting and/or the like). As a result, the electric stimulation applied to, for example, the peroneal nerve is terminated and/or modulated, thereby allowing the set of muscles associated therewith to relax. Thus, the foot of the impaired leg can pivot about the ankle away from the leg (i.e., plantarflexion). In this manner, the FES orthosis can provide functional electrical stimulation that can enhance the function of the impaired leg to facilitate gait.

Although the method 1000 described above includes the electric stimulator receiving a first signal and a second signal from the sensor, in some instances, the sensor can be configured to send any number of signals to the electric stimulator that can be, for example, associated with adjusting one or more parameters of the electric stimulation provided to the neuromuscular system of the limb. By way of example, in some instances, the sensor can send the signal to the electric stimulator (i.e., at 1003) and can be configured to sense and/or otherwise detect an amount of the dorsiflexion and/or inversion or eversion of the foot in response to the electric stimulation and based on the sensed and/or detected characteristic, can send one or more signals to the electric stimulator (i.e., prior to the signal sent at 1004) associated with adjusting one or more parameters of the electric stimulation (e.g., a voltage provided to one or more portions of the electrode assembly and/or the like).

Although the method 1000 described above includes the electric stimulator terminating and/or modulating the electric stimulation based on receiving the second signal from the sensor, in some instances, the electric stimulator can terminate and/or modulate the electric stimulation based on any set of signals, parameters, history, and/or the like. For example, in some instances, the electric stimulator can receive the second signal from the sensor and can compare data included in and/or represented by the second signal with historical data such as, for example, a previous gait event and/or the like. As such, the electric stimulator can be configured to adjust, terminate, and/or modulate the electric stimulation provided to the portion of the neuromuscular based at least in part on the second signal and/or any other data associated with a gait event, characteristic, and/or parameter.

Figure 10:
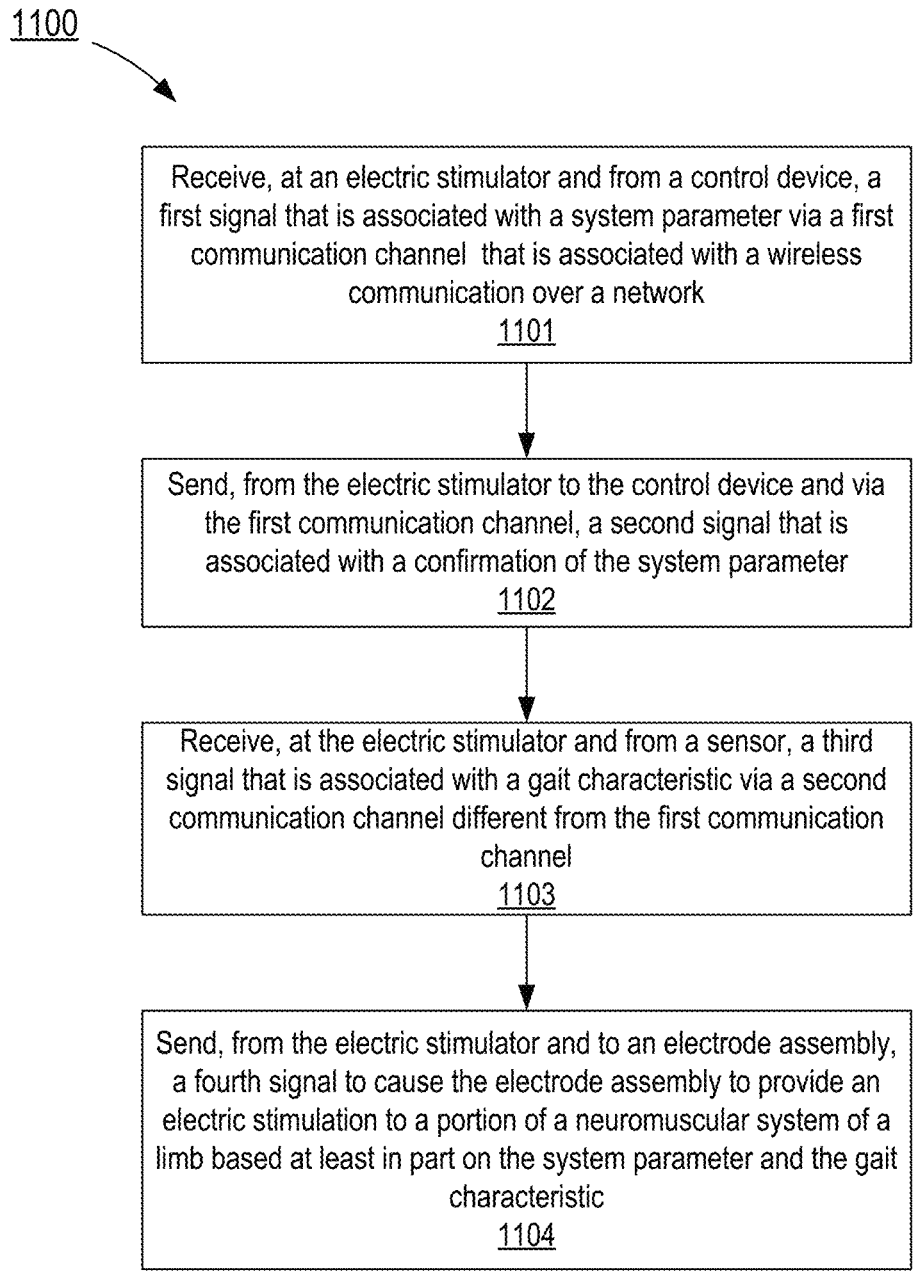
FIG. 10 is a flowchart illustrating a method of using an FES system for gait modulation according to an embodiment.

FIG. 10 is a flowchart illustrating a method 1100 of using an FES orthosis for gait modulation according to an embodiment. The FES orthosis can be any suitable neuroprosthetic and/or the like such as the orthosis 100 and/or 200 described herein. As such, the orthosis can include a frame, an electrode assembly, a sensor, and an electric stimulator, and can be coupled to and/or disposed about an impaired leg of a patient to provide FES thereto. The method 1100 includes receiving, at the electric stimulator and from a control device, a first signal that is associated with a system parameter via a first communication channel, at 1101. The control device can be any suitable device such as, for example, the control devices 160, 260, and/or 260' described herein. The first communication channel can be associated with a wireless communication over a network. For example, the electric stimulator can include a communication device such as the communication device 248 in FIG. 7, which can communicate with one or more electronic devices. The network and the communication channel can be any suitable network and communication channel, respectively, such as those described herein. By way of example, in some embodiments, the network can be a personal area network (PAN) and the communication channel can be associated with Bluetooth®.

In some embodiments, the system parameter can be associated with, for example, an initialization of the FES orthosis. For example, in some embodiments, the patient can be receiving FES therapy for the first time and as such, system parameters and/or settings of the FES orthosis may not be appropriately defined for the patient. As such, a health care provider can manipulate the control device (e.g., a smart phone, a PC, a tablet, etc.) to define an initial set of system characteristics and/or a second of calibration parameters for the FES orthosis that are uniquely established for the patient. In some instances, with the first communication channel being associated with a wireless communication over a network, a health care professional can manipulate the control device to define the system parameter substantially remotely (e.g., at a location physically distinct from the FES orthosis). By way of example, the health care professional can be at a medical facility and can manipulate the control device to define the system parameter and can send the first signal via, for example, a LAN and the Internet to the FES orthosis worn by a patient that is at his or her home (or any other location other than the medical facility). Upon receipt of the first signal, a second signal that is associated with a confirmation of the system parameter is sent from the electric stimulator to the control device, at 1102. In some embodiments, the second signal can be sent in a similar manner as described with reference to the first signal.

The electric stimulator receives a third signal that is from the sensor via a second communication channel, different from the first communication channel, at 1103. The sensor can be substantially similar in form and function as the sensor 230 described above with reference to FIG. 7. In this manner, the sensor can include one or more sensing devices such as, for example, a tilt sensor, pressure sensor, accelerometer, gyroscope, etc. that can sense and/or detect the gait characteristic. In some embodiments, the gait characteristic can be associated with, for example, a "heel-off" event or the like of the impaired leg (e.g., a decrease in pressure as a result of the heel being lifted away from a surface upon which the patient is walking and/or any other suitable characteristic). In other embodiments, the gait characteristic can be associated with any suitable gait event.

Based at least in part on the system parameter and the gait characteristic, a fourth signal is sent, from the electric stimulator to the electrode assembly, to cause the electrode assembly to provide an electric stimulation to a portion of a neuromuscular system of the limb (e.g., the impaired leg), at 1104. For example, in some embodiments, the FES orthosis can be disposed about and/or can at least partially envelop a portion of the impaired leg to substantially align and/or otherwise place one or more electrodes included in the electrode assembly in electrical communication with, for example, the peroneal nerve of the impaired leg. Thus, electric stimulation is provided to a set of muscles associated with the portion of the neuromuscular system of the impaired leg, resulting in dorsiflexion of the foot of the impaired leg (i.e., a pivoting of the foot substantially about the ankle towards the leg). Thus, the FES orthosis can be used to enhance limb function of the impaired leg to mitigate the effects of, for example, lower leg paralysis such as drop foot or the like.

Although the embodiments and methods have been described above as providing functional electrical stimulation to an impaired leg of a patient experiencing, for example, drop foot, in other embodiments, the embodiments and methods can be used to enhance the function of any suitable limb or other portion of the body. By way of example, in some embodiments, an FES orthosis can include a frame, an electrode assembly, a sensor, and an electric stimulator and can be adapted to enhance the function of a patients hand or the like. In some instances, the sensor of such FES orthosis can be configured to sense and/or detect one or more characteristics associated with the function of the hand and can send a signal to the electric stimulator (in a similar manner as described above) that is associated with the one or more characteristics. As such, the electric stimulator can generate an electrical current that can be transmitted through one or more electrodes included in the electrode assembly, thereby providing FES to one or more nerves associated with the function of the hand.

While the embodiments and methods have been described above as including an electrode assembly that is physically coupled to an FES orthosis and that is disposed adjacent to an external surface of the body of a patient, in other embodiments, an FES orthosis can include and/or can otherwise be coupled to an electrode assembly that can be at least partially disposed within a portion of the body of the patient. For example, in some embodiments, an FES orthosis can be operably coupled to an electrode assembly that includes electrodes disposed within the body of a patient. In some embodiments, at least a portion of the electrode assembly can be disposed within the body in such a manner that the electrodes are disposed adjacent to and/or in electrical communication with, for example, the peroneal nerve, the tibial nerve, and/or any other suitable portion of a neuromuscular system of the patient. In some embodiments, the electrode assembly can include one or more external connectors configured to place the electrodes disposed within the body in electrical communication with an electric device that is disposed externally of the body. In other embodiments, the electrode assembly need not include such connectors and can transmit a flow of electrical current via, for example, inductive coupling and/or the like.

Although the embodiments and methods have been described above as including a sensor that can be integrate into an FES orthosis and/or that can be coupled to a structure substantially outside of the body (e.g., a shoe, the orthosis, etc.), in other embodiments, an FES orthosis can include and/or can otherwise be in communication with one or more sensors disposed within the body of a patient. For example, in some embodiments, a relatively small sensor can be subcutaneously implanted into a portion of the patient's foot, ankle, lower leg, upper leg, and/or any other suitable portion of the body.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain of the events may be performed concurrently in a parallel process when possible, as well as performed sequentially as described above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

What is claimed is:

1. A method, comprising:
    receiving, at an electric stimulator and from a plurality of sensors, a plurality of signals associated with a gait characteristic at a first time, the electric stimulator being removably coupled to a frame assembly that is removably coupleable to a portion of a limb, the gait characteristic associated with at least one of a position relative to the frame assembly of each of at least two sensors from the plurality of sensors or a position relative to a reference plane of each limb segment from a plurality of limb segments of the limb;
    calculating, via a processor coupled to the electric stimulator, one or more system parameters based at least in part on the plurality of signals associated with the gait characteristic at the first time; and
    sending a signal based at least in part on the one or more system parameters, from the electric stimulator to an electrode assembly, to cause the electrode assembly to provide an electric stimulation to a portion of a neuromuscular system of the limb.

2. The method of claim 1, wherein the position relative to the reference plane is an angular position relative to the reference plane.

3. The method of claim 1, wherein the plurality of sensors are disposed at the plurality of limb segments.

4. The method of claim 1, wherein the at least two sensors includes:
    a first sensor from the plurality of sensors disposed at a first limb segment, the first limb segment associated with one of a foot, ankle, lower leg, or upper leg, and
    a second sensor from the plurality of sensors disposed at a second limb segment different from the first limb segment, the second limb segment associated with one of the foot, ankle, lower leg or upper leg.

5. The method of claim 1, wherein at least a first sensor from the plurality of sensors is coupled to the frame assembly.

6. The method of claim 1, wherein at least a first sensor from the plurality of sensors is at least partially integrated with the electric stimulator and at least a second sensor from the plurality of sensors is physically distinct from the electric stimulator.

7. The method of claim 1, wherein the electric stimulator is in wireless electrical communication with a control device, the calculating one or more system parameters includes calculating one or more system parameters defined by the control device.

8. The method of claim 1, wherein the receiving of the plurality of signals includes receiving at least a first signal via a wireless communication mode.

9. The method of claim 1, further comprising:
receiving, at the electric stimulator and from at least one sensor from the plurality of sensors, a signal associated with the gait characteristic at a second time subsequent the first time; and
terminating the electric stimulation of the portion of the neuromuscular system of the limb based on the receiving of the signal associated with the gait characteristic at the second time subsequent the first time.

10. The method of claim 1, wherein the sending the signal from the electric stimulator to the electrode assembly to cause the electrode assembly to provide an electric stimulation to a portion of a neuromuscular system of a limb is associated with a heel-off event during ambulatory motion of the limb.

11. The method of claim 10, further comprising:
receiving, at the electric stimulator and from at least one sensor from the plurality of sensors, a signal associated with the gait characteristic at a second time subsequent the first time; and
terminating the electric stimulation of the portion of the neuromuscular system of the limb based on the receiving of the signal associated with the gait characteristic at the second time subsequent the first time, the gait characteristic at the second time associated with a heel-on event during the ambulatory motion of the limb.

12. The method of claim 1, wherein the receiving the first signal associated with the first characteristic is at a first time;
the receiving the second signal associated with the second characteristic is at the first time.

13. The method of claim 1, wherein:
the at least two sensors includes a first sensor and a second sensor,
the first sensor includes one of a tilt sensor, an accelerometer, or a gyroscope, and
the second sensor includes one of a tilt sensor, an accelerometer, or a gyroscope.

14. A method, comprising:
receiving, at an electric stimulator and from a first sensor of a plurality of sensors, a first signal associated with a gait characteristic, the first sensor being one of a tilt sensor, an accelerometer, or a gyroscope, the first sensor being coupled to a limb at a first location of the limb;
receiving, at the electric stimulator and from a second sensor of the plurality of sensors, a second signal associated with the gait characteristic, the first sensor being one of a tilt sensor, an accelerometer, or a gyroscope, the second sensor being coupled to the limb segment at a second location of the limb different than the first location;
calculating, via a processor coupled to the electric stimulator, one or more system parameters based at least in part on the first signal and the second signal;
sending a signal, based at least in part on the one or more system parameters, from the electric stimulator to an electrode assembly to cause the electrode assembly to provide an electric stimulation to a portion of a neuromuscular system of a limb;
receiving, at the electric stimulator and from one of the first sensor or the second sensor, a third signal associated with the gait characteristic; and
terminating the electric stimulation of the portion of the neuromuscular system of the limb based on the receiving of the third signal associated with the gait characteristic.

15. The method of claim 14, wherein one of the first sensor or the second sensor is at least partially integrated with the electric stimulator.

16. The method of claim 14, wherein the electric stimulator is in wireless electrical communication with a control device, the calculating one or more system parameters includes calculating one or more system parameters defined by the control device.

17. The method of claim 14, wherein the sending the signal from the electric stimulator to the electrode assembly to cause the electrode assembly to provide an electric stimulation to a portion of a neuromuscular system of a limb is associated with a heel-off event during ambulatory motion of the limb; and
the terminating the electric stimulation of the portion of a neuromuscular system of the limb is associated with a heel-on event during the ambulatory motion of the limb.

18. The method of claim 14, wherein:
the receiving the first signal associated with the gait characteristic is at a first time,
the receiving the second signal associated with the gait characteristic is at the first time,
the receiving the third signal associated with the gait characteristic is at a second time, after the first time, and
the sending the signal to the electrode assembly to cause the electrode assembly to provide the electric stimulation to the portion of the neuromuscular system of the limb includes providing the electric stimulation during a time period defined between the first time and the second time.

* * * * *